United States Patent
Wang et al.

(10) Patent No.: US 10,864,179 B2
(45) Date of Patent: Dec. 15, 2020

(54) HISTONE DEACETYLASE INHIBITORS FOR THE USE IN THE TREATMENT OF DRUG RESISTANT MELANOMA

(71) Applicant: STICHTING HET NEDERLANDS KANKER INSTITUUT-ANTONI VAN LEEUWENHOEK ZIEKENHUIS, Amsterdam (NL)

(72) Inventors: Liqin Wang, Amsterdam (NL); Rodrigo Leite De Oliveira, Amsterdam (NL); Rene Bernards, Amsterdam (NL)

(73) Assignee: STICHTING HET NEDERLANDS KANKER INSTITUUT-ANTONI VAN LEEUWENHOEK ZIEKENHUIS, Amsterdam (NL)

( * ) Notice: Subject to any disclaimer, the term of this patent is extended or adjusted under 35 U.S.C. 154(b) by 0 days.

(21) Appl. No.: 15/764,781

(22) PCT Filed: Sep. 8, 2016

(86) PCT No.: PCT/NL2016/050625
§ 371 (c)(1),
(2) Date: Mar. 29, 2018

(87) PCT Pub. No.: WO2017/058007
PCT Pub. Date: Apr. 6, 2017

(65) Prior Publication Data
US 2018/0280324 A1    Oct. 4, 2018

(30) Foreign Application Priority Data
Oct. 1, 2015   (NL) .................................. 2015539

(51) Int. Cl.
| | |
|---|---|
| *A61K 31/167* | (2006.01) |
| *A61K 31/454* | (2006.01) |
| *A61K 31/4406* | (2006.01) |
| *A61K 31/4184* | (2006.01) |
| *A61K 31/506* | (2006.01) |
| *A61K 31/4045* | (2006.01) |
| *A61K 31/18* | (2006.01) |
| *A61K 31/15* | (2006.01) |
| *A61P 35/00* | (2006.01) |
| *A61K 45/06* | (2006.01) |
| *A61K 31/635* | (2006.01) |
| *A61K 31/437* | (2006.01) |
| *A61K 31/713* | (2006.01) |
| *A61K 31/519* | (2006.01) |
| *A61K 38/15* | (2006.01) |
| *A61K 31/517* | (2006.01) |

(52) U.S. Cl.
CPC ............ *A61K 31/167* (2013.01); *A61K 31/18* (2013.01); *A61K 31/4045* (2013.01); *A61K 31/4184* (2013.01); *A61K 31/437* (2013.01); *A61K 31/4406* (2013.01); *A61K 31/454* (2013.01); *A61K 31/506* (2013.01); *A61K 31/519* (2013.01); *A61K 31/635* (2013.01); *A61K 31/713* (2013.01); *A61K 38/15* (2013.01); *A61K 45/06* (2013.01); *A61P 35/00* (2018.01); *A61K 31/517* (2013.01); *A61K 2300/00* (2013.01)

(58) Field of Classification Search
CPC .............................. A61K 31/167; A61P 35/00
See application file for complete search history.

(56) References Cited

U.S. PATENT DOCUMENTS

| | | | |
|---|---|---|---|
| 2015/0056192 A1* | 2/2015 | Chaturvedi ............ | A61K 38/00 424/133.1 |
| 2015/0283136 A1* | 10/2015 | Gallagher .............. | A61K 45/06 514/275 |

FOREIGN PATENT DOCUMENTS

| | | | | |
|---|---|---|---|---|
| EP | 2916834 | | 9/2015 | |
| EP | 2916834 A1 * | | 9/2015 | ............. A61K 45/06 |
| WO | WO-2013151638 A1 * | | 10/2013 | ......... A61K 31/5517 |
| WO | WO-2014072493 A1 * | | 5/2014 | ............. A61K 45/06 |

OTHER PUBLICATIONS

Haas et al. Invest New Drugs, (2014), V32, p. 526-534.*
Lai et al. Advances in Pharmacology, (2012), v.65, p. 27-43.*
International Search Report and Written Opinion, International Patent Application No. PCT/NL2016/050625, dated Nov. 25, 2015.
Jazirehi Ali R. et al. "Aberrant apoptotoic machinery confers melanoma dual resistance to BRAF (V600E) inhibitor and immun effector cells: Immunosensitization by a histone deacetylase inhibitor" Am J Clin Exp Immunol, vol. 3, No. 1, Jan. 1, 2014, pp. 43-56.
Lai F. et al. "Cotargeting histone deacetylases and oncogenic BRAF synergistically kills human melanoma cells by necrosis independently of RIPK1 and RIPK3" Cell Death & Disease, Nature publishing group, GB, vol. 4, Jun. 6, 2013, pp. e655-1.

* cited by examiner

*Primary Examiner* — Yong L Chu
(74) *Attorney, Agent, or Firm* — Casimir Jones, S.C.; Robert A. Goetz

(57) ABSTRACT

The current invention relates to treatment of drug resistant melanoma with histone deacetylase inhibitors (HDACi). In particular the invention relates to BRAF and NRAS mutated melanoma and that have acquired resistance to MAPK pathway inhibitors, for example due to previous treatment with such MAPK pathway inhibitors. The invention discloses HDACi and/or MAPK pathway inhibitors for use in such treatment and treatment regimens using such inhibitors.

7 Claims, 25 Drawing Sheets
Specification includes a Sequence Listing.

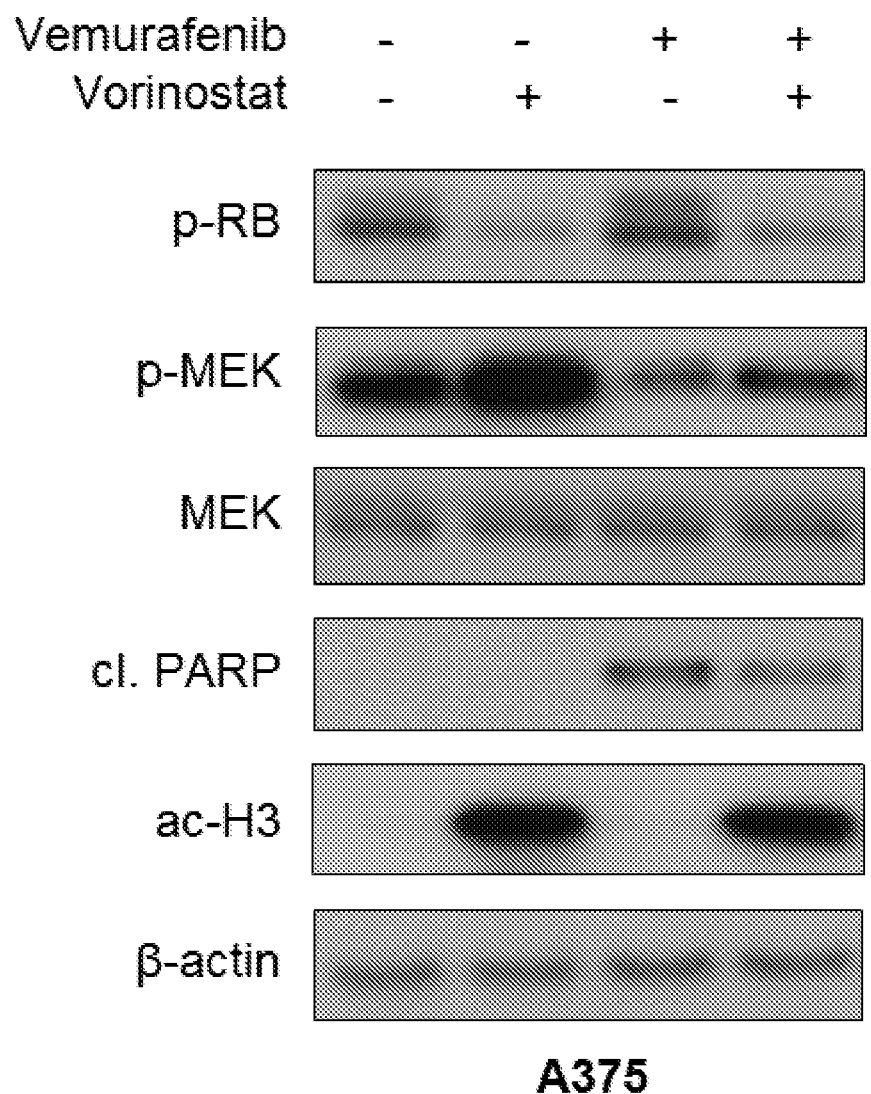

A)

B)

C)

Figure 9:
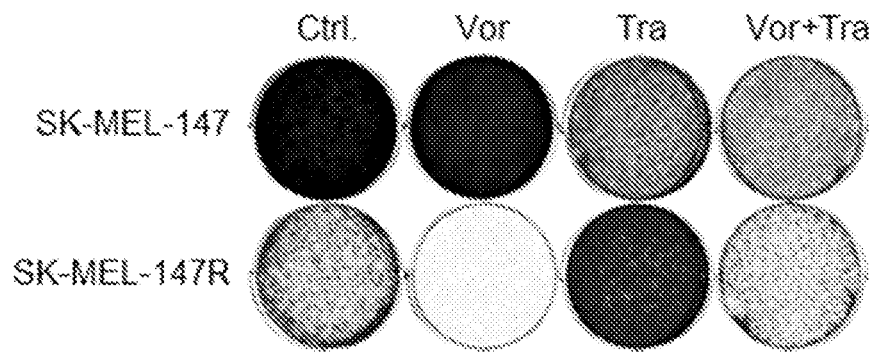
Figure 9:
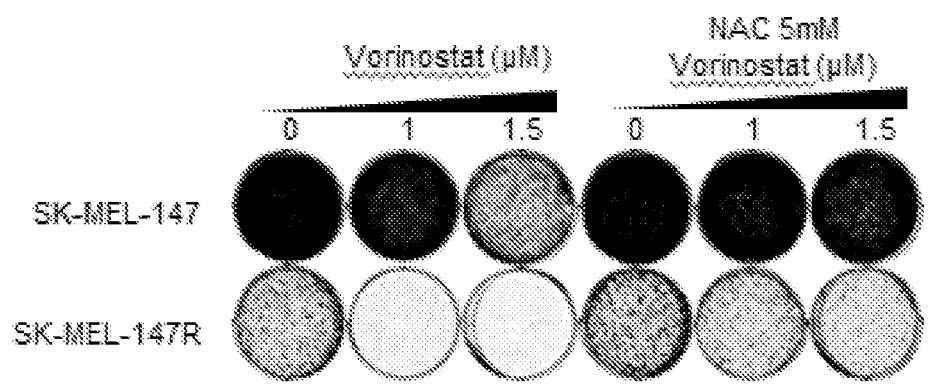
Figure 9:
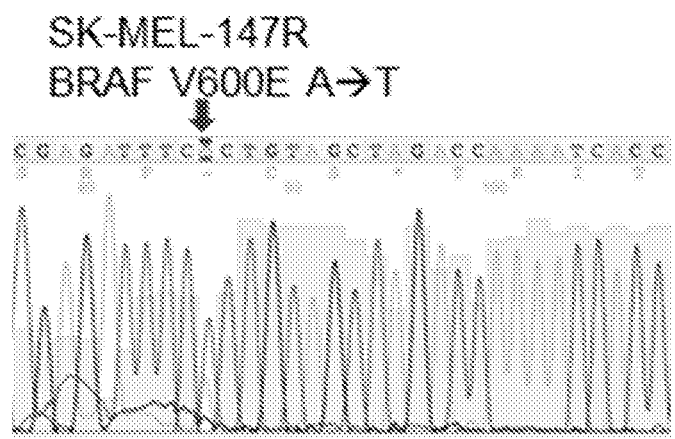

Fig. 9 – continued
D)
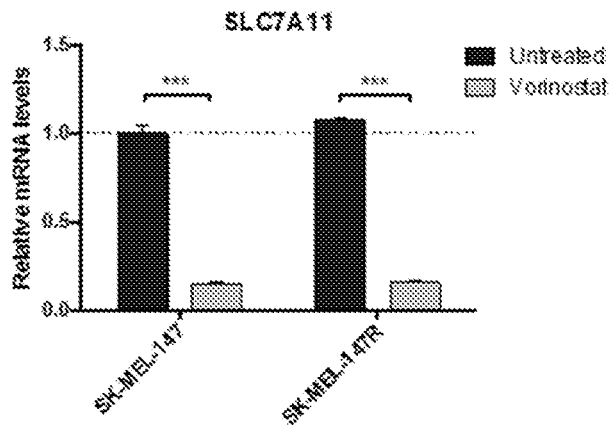
E)
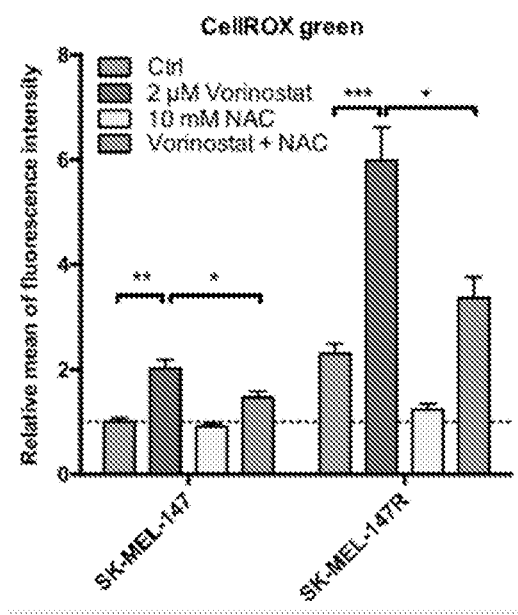
F)
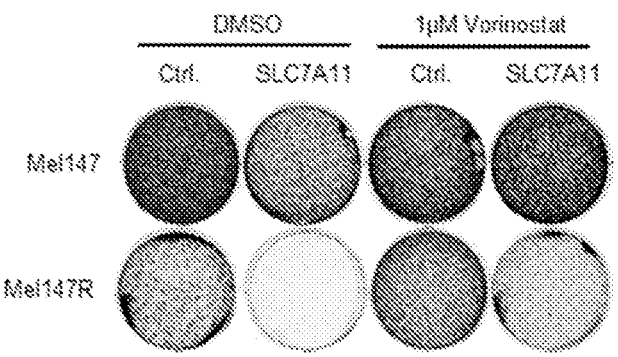

Fig. 9 – continued
G)
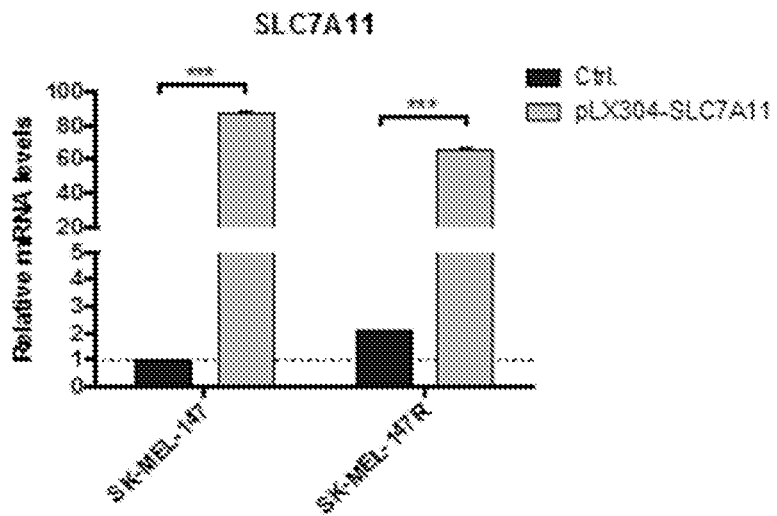
H)
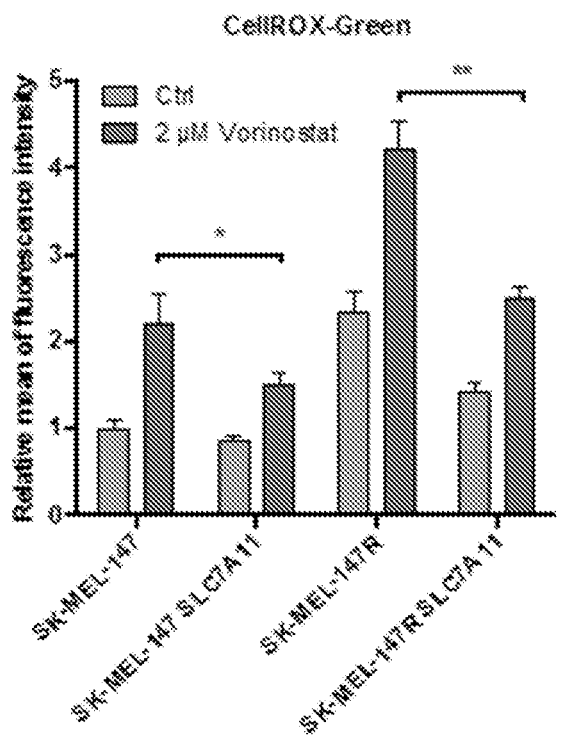

Fig. 9 – continued
I)
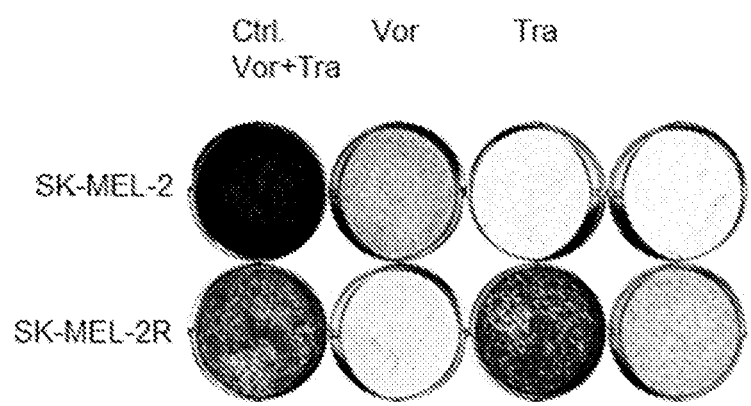
J)
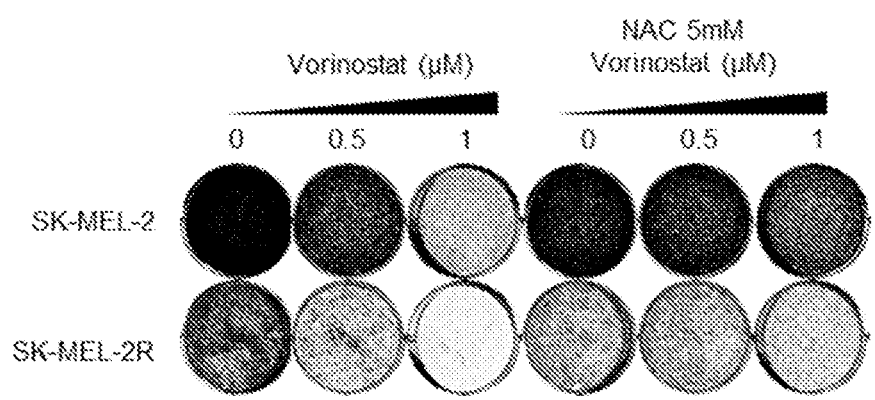

A)

B)

C)

Figure 10:
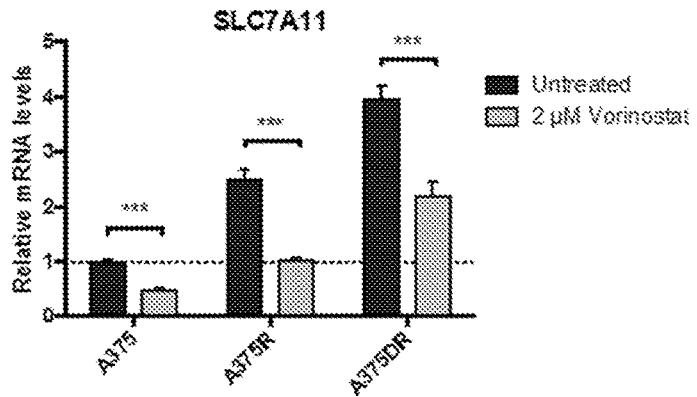
Figure 10:
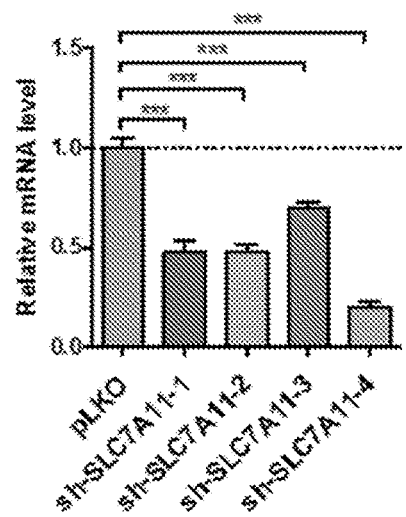
Figure 10:
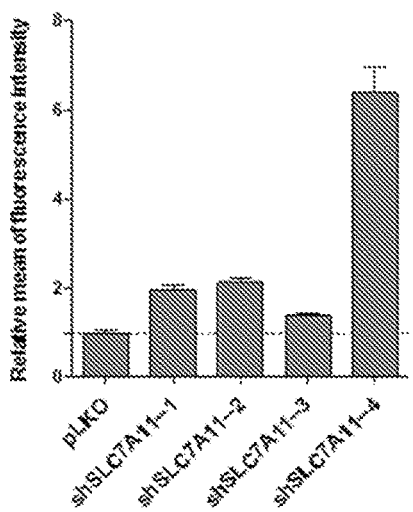

Fig. 10 – continued
D)
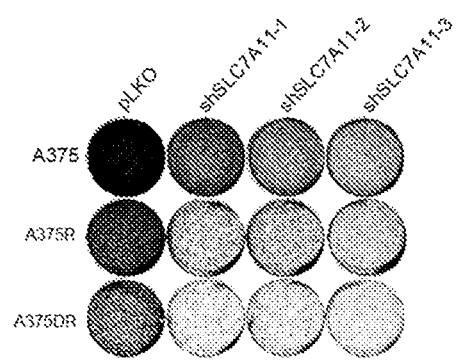
F)
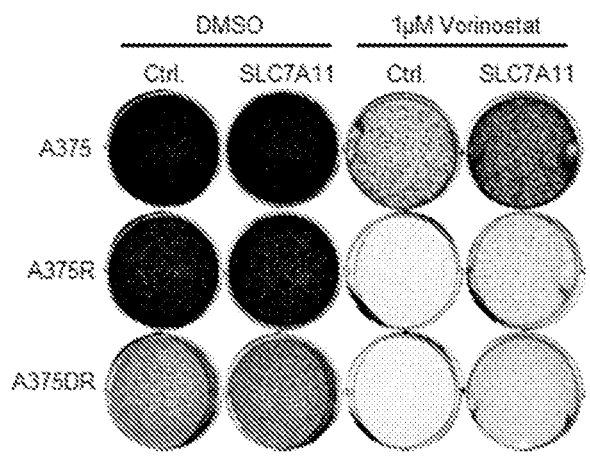

Fig. 10 – continued
E)
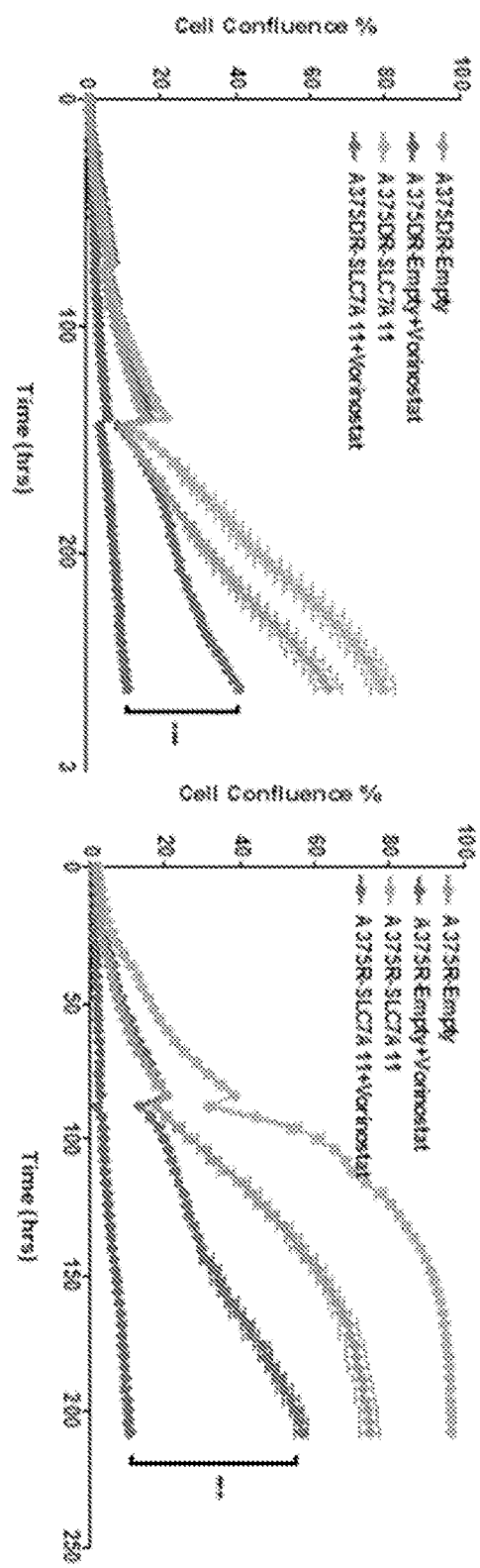

Fig. 10 – continued
G)
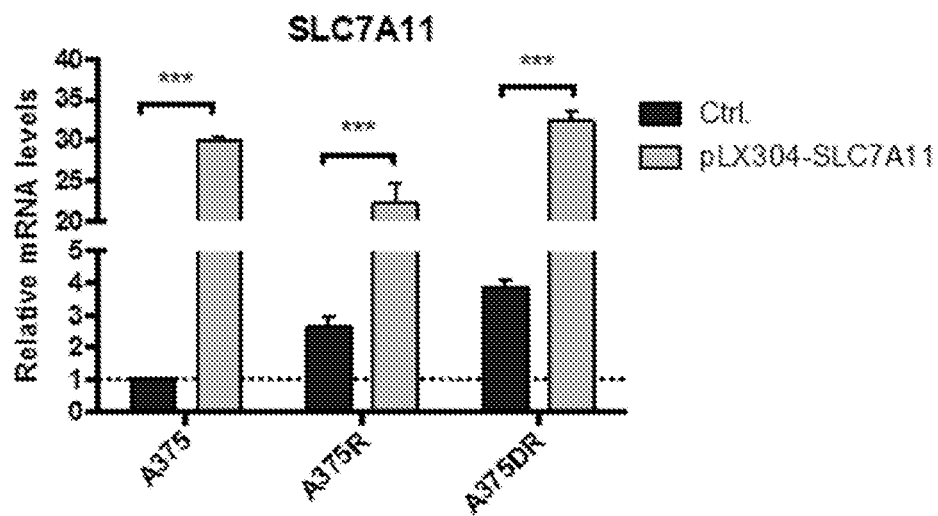
H)
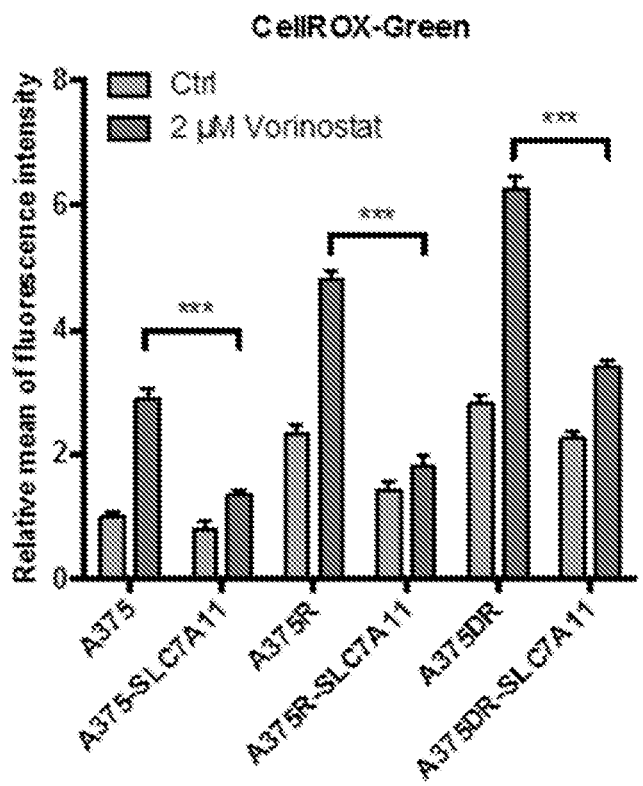

HISTONE DEACETYLASE INHIBITORS FOR THE USE IN THE TREATMENT OF DRUG RESISTANT MELANOMA

PRIOR ART

Cancer is one of the leading causes of death in the Europe and the United States. Despite recent advances in understanding mechanisms involved in cancer and in diagnosis and treatment, drug therapies for metastatic disease are often palliative in nature. Drug therapies seldom offer a long-term cure. There is a constant need for new methods of treatment, either in the form of monotherapy or in the form of combination treatment, combining different new or known drugs, for example as first line therapy.

Cancer cells are by definition heterogeneous. For example, multiple mutational mechanisms may lead to the development of cancer and mutational mechanisms associated with some cancers may differ between one tissue type and another; it is therefore often difficult to predict whether a specific cancer will respond to a specific chemotherapeutic (Cancer Medicine, 5th edition, Bast et al, B. C. Decker Inc., Hamilton, Ontario).

The treatment of cancer is gradually changing from an organ-centered to a pathway-centered approach. Cancer cells often have an addiction to the signals that are generated by the cancer-causing genes. Consequently, targeted cancer drugs that selectively inhibit the products of activated oncogenes can have dramatic effects on cancer cell viability. This approach has yielded significant clinical results for Non-Small Cell Lung Cancer (NSCLC) having activating mutations in EGFR or translocations of the ALK kinase. However, this approach has not been successful in all type of cancers, in particular in cancers characterized by oncogenic mutations in RAS genes.

Melanoma is a malignant tumor of melanocytes. It is one of the rarest forms of skin cancer but accounts for the majority of skin cancer deaths. Despite many years of intensive research, the only effective treatment is surgical resection of the primary tumor before it reaches a thickness of more than 1 mm. According to a WHO report, there are approximately 48,000 melanoma deaths each year, and about 160,000 new cases of melanoma are diagnosed yearly. It occurs more frequent in women than in men and is particularly common among Caucasians living in sunny climates, with high rates of incidence in Australia, New Zealand, North America, Latin America, and northern Europe.

Treatment of melanoma typically includes surgical removal of the melanoma, adjuvant treatment, chemo- and immunotherapy, and/or radiation therapy. The chance of a cure is greatest when the melanoma is discovered while it is still small and thin, and can be removed entirely.

Approximately 40-60% of (cutaneous) melanomas carry a mutation in the protein kinase referred to as BRAF. Approximately 90% of these mutations result in the substitution of glutamic acid for valine at codon 600 (BRAF V600E) although other mutations are also known (e.g. BRAF V600K and BRAF V600R). Such mutations in BRAF typically leads to proliferation and survival of melanoma cells (Davies et al Nature 2002; 417:949-54; Curtin et al N Engl J Med 2005; 353:2135-47) through activation of the MAPK pathway. This pathway plays a significant role in modulating cellular responses to extracellular stimuli, particularly in response to growth factors, and the pathway controls cellular events including cell proliferation, cell-cycle arrest, terminal differentiation and apoptosis (Peyssonnaux et al., Biol Cell. 93(I-2):53-62 (2001)).

The discovery of the common BRAFV600E mutation in melanoma has resulted in the development of targeted therapies, which are associated with unprecedented clinical benefits. The small molecule inhibitor vemurafenib, specifically targeting the mutant BRAF kinase, for example, had become standard of care for patients diagnosed with mutant BRAF metastatic melanoma. However, although this compound initially reduces tumor burden dramatically, eventually melanomas become resistant and patients progress in the disease (Wagle et al. J Clin Oncol. 29(22):3085-96 (2011); Fedorenko et al (2015) BJC 112, 217-226. doi: 10.1038/bjc.2014.476).). Another example is NRAS mutations or NRAS mutated cancers. Among the first oncogenes discovered in cutaneous melanoma was NRAS, which is mutant in up to 20% of tumors causing aberrant signaling in several downstream cascades. Despite, being a highly relevant therapeutic target, design of small molecules selectively inhibiting mutant NRAS to date, remains an unresolved challenge. The majority of NRAS mutations are found in codon 61 impairing the enzymatic activity of RAS to cleave GTP to GDP. Other, less frequent mutations are found in codon 12 and 13 preventing the association of GAPase activating proteins (GAP), which accelerate the weak hydrolytic potential of RAS. As a result, NRAS remains in its active, GTP-bound state driving cell proliferation, survival and motility making NRAS an important therapeutic target (Posch, Oncotarget (2013) 4(4):494-5).

Despite strong preclinical evidence for treating NRAS-mutant melanoma using inhibitors of MEK, clinical trials so far have demonstrated only modest activity in patients. At first, early generation MEK inhibitors exhibited only a 10% objective response rate. However, excitement at the idea of targeting MEK resurfaced with the development of potent third-generation MEK inhibitors trametinib (GSK1120212) and MEK162 (ARRY-438162). In the recent phase II clinical trial of MEK162, 20% of NRAS-mutant patients exhibited objective responses while a further 43% showed stable disease. A phase III trial is currently ongoing comparing MEK162 with dacarbazine specifically in NRAS-mutant metastatic melanoma patients (Fedorenko et al (2015) BJC 112, 217-226. doi:10.1038/bjc.2014.476).

However, (acquired) drug resistance to inhibitors of the MAPK pathway, i.e. a RAS inhibitor, a RAF inhibitor, a MEK inhibitor, an ERK inhibitor and/or a RSK inhibitor, in melanoma almost invariably limits the duration of clinical benefit of treatments with single compounds or combinations (Seton-Rogers et al. Nature Reviews Cancer 14, 7 (2014) doi:10.1038/nrc3653; Van Allen et al. Cancer Discov. http://dx.doi.org/10.1158/2159-8290.CD-13-0617 (2013)).

This highlights the urgent need to develop strategies to treat melanomas that have developed resistance to MAPK pathway inhibitors.

DESCRIPTION

Summary of the Invention

The present invention relates to a histone deacetylase inhibitor (HDACi) for use in the treatment of a subject with melanoma. The melanoma is characterized in that the melanoma is a BRAF-mutation or a NRAS-mutation harboring melanoma and has acquired resistance to one or more mitogen-activated protein kinase (MAPK) pathway inhibitors, such as a RAS inhibitor, a RAF inhibitor, a MEK inhibitor, an ERK inhibitor and/or a RSK inhibitor. In the treatment with the HDACi no MAPK pathway inhibitor is used.

The present invention also relates to methods of treating a subject with melanoma characterized in that the melanoma is a BRAF-mutation or a NRAS-mutation harboring melanoma, the method comprising:

a) Treating said subject with a therapeutically acceptable amount of a MAPK pathway inhibitor;
b) Discontinuing treating the subject with said therapeutically acceptable amount of a MAPK pathway inhibitor when the melanoma has acquired resistance to a MAPK pathway inhibitor;
c) Treating said subject with a therapeutically acceptable amount of a HDACi.

Recently it has been suggested that a combination of BRAF inhibitors and inhibitors of histone deacetylases (histone deacetylase inhibitors; HDACi) can result in more durable responses in BRAF mutant melanoma patients (Johannessen et al. Nature 504, 138-142 (2013); Lai et al., Cell Death and Disease (2013) 4, e655; doi:10.1038/cddis.2013.192).

European patent application EP2916834 likewise suggests a combined treatment with a BRAF inhibitor and a histone deacetylases inhibitor. According to EP2916834 the histone deacetylase inhibitor sensitizes melanoma cells to B-Raf induced death. EP2916834 requires the patient to be treated with the combination of the HDACi and the BRAF inhibitor such that they are jointly therapeutically active (at the same time), meaning that the therapeutic agents should be given in such time intervals that the combination shows an interaction of the BRAF inhibitor and the HDACi (i.e. allows for a simultaneous effect of the BRAF inhibitor and the HDACi).

We show here that, surprisingly, MAPK inhibitors (MAPKi) and HDACi, for example BRAF inhibitors and HDAC inhibitors, have antagonistic effects when used in combination in melanoma, resulting in a limited anti-cancer effect. At the same time, and in contrast to suggestions in the prior art, we have established that sequential treatment of melanomas that have acquired resistance to a MAPK pathway inhibitor with HDACi leads to a prolonged state of proliferation arrest and cell death, which ultimately leads to regression of the MAPK pathway inhibitor resistant tumor. Mechanistically, we find that the hyperactivation of the MAP kinase pathway, which is induced through the development of resistance to the MAPK pathway inhibitors, is maintained by the sequential treatment with HDACi and is detrimental to the cancer cells. The term "sequential treatment with HDACi" as used herein refers to a situation where the treatment with a HDACi takes place after the treatment with a MAPK pathway inhibitor, i.e. separately or not simultaneously or not at the same time as the treatment with a MAPK pathway inhibitor, e.g. after the treatment with a MAPK pathway inhibitor has been discontinued or stopped. In other words, the HDACi and the MAPK pathway inhibitor are not or cannot be jointly therapeutically active in the patient receiving the treatment. In other words, the treatment (=e.g. having a therapeutic effect) with the MAPK inhibitor is not simultaneous with the treatment with the HDACi.

Our data indicates that simultaneous treatment of BRAF mutant melanoma with a combination of BRAF and HDAC inhibitors is not beneficial, but that a sequential treatment first with MAPK pathway inhibitors and followed by a switch to HDAC inhibitor (i.e. discontinuing treatment with the MAPK pathway inhibitor) once resistance to the MAPK pathway inhibitors has developed or is developing, results in durable responses in MAPK pathway inhibitor resistant melanomas.

The present invention is based on the surprising finding that in melanoma harboring a BRAF-mutation or in melanoma harboring a NRAS-mutation a sequential treatment with a MAPK pathway inhibitor, followed by a switch to treatment with a HDACi (and discontinuing treatment with a/the MAPK pathway inhibitor) once the melanoma acquires resistance to a MAPK pathway inhibitor results in better and improved treatment of MAPK pathway inhibitor resistant melanomas. The response of the melanoma to the sequential treatment (i.e. the HDACi and the MAPK pathway inhibitor are not or cannot be jointly/at the same time therapeutically active in the patient) is better than with simultaneous treatment with a MAPK pathway inhibitor and a HDACi (the HDACi and the MAPK pathway inhibitor are jointly therapeutically active in the patient), the latter combination showing antagonistic effects resulting in a limited anti-cancer effect.

Where the prior art, including EP2916834, suggests the combined treatment of a BRAF inhibitor and a HDACi, allowing the inhibitors to interact in the patients therewith being jointly therapeutically active (i.e. giving a combined and simultaneous therapeutic effect), the present inventors found that improved results are obtained by treating BRAF-mutated or NRAS-mutated melanoma that acquired resistance to a MAPK pathway inhibitor with a HDACi under conditions that the HDACi and the MAPK pathway inhibitor are not "jointly therapeutically active" in the patient. In the practice of the inventions this means that a melanoma is first treated with a MAPK pathway inhibitor. Once the melanoma acquires resistance to the MAPK pathway inhibitor or has become resistant to the MAPK pathway inhibitor, treatment with the MAPK pathway inhibitor is discontinued, meaning that the patient is no longer provided with therapeutically acceptable amounts of a MAPK pathway inhibitor. After the treatment with the MAPK pathway inhibitor is discontinued, treatment with the HDACi is started, meaning that therapeutically acceptable amounts of an HDACi are provided to the patient (in other words, the patient is provided with an amount of at least one compound with the purpose of inhibiting the activity of histone deacetylase in the patient with the aim of inducing or contributing to inducing a therapeutic effect). As a consequence of the discontinued treatment with the MAPK pathway inhibitor, the HDACi and the MAPK pathway inhibitor will no longer interact in the patient (i.e. the HDACi and the MAPK pathway inhibitor are not jointly therapeutically active in the patient), therewith preventing the antagonist effect of the combination observed by the current inventors. The HDACi, in absence of the MAPK pathway inhibitor was found to provide for effective and durable anti-cancer effects in the BRAF and/or NRAS mutilation harboring melanoma that acquired resistance to the MAPK pathway inhibitor or that are resistant to a MAPK pathway inhibitor.

It was observed that treatment with HDACi caused the down-regulation (reduced levels) of a protein known in the art as XCT (or xCT) in the melanoma cells, which in turn caused an increase in ROS levels in said cells, ultimately causing them to die (reduced cell survival). This effect was found to be surprisingly more pronounced in melanoma cells resistant to MAPK pathway inhibitor therapy. XCT is part of the so-called xc-system, a cell-surface Na+-independent cystine-glutamate antiporter composed of the 12-pass transmembrane transporter protein SLC7A11 (xCT) linked via a disulfide bridge to the single-pass transmembrane regulatory subunit SLC3A2 (4F2hc). System xc- is required for normal mammalian blood plasma redox homeostasis, skin pigmentation, immune system function, and memory formation (see, e.g. Dixon et al (2014) eLife. 3: e02523 doi: 10.7554/eLife.02523)

It was surprisingly found that treatment with a XCT inhibitor (XCTi), e.g. sulfasalazine or erastatin, mimicked the effects of HDACi treatment on melanoma cells, i.e. increased cell death (or decreased survival). This effect was found to be surprisingly more pronounced in melanoma cells resistant to MAPK pathway inhibitor therapy. Thus, in other words, the present invention is also based on the surprising finding that in melanoma harboring a BRAF-mutation or in melanoma harboring a NRAS-mutation a sequential treatment with a MAPK pathway inhibitor, followed by a switch to treatment with a xTC inhibitor (alone or in combination with a HDACi) (and discontinuing treatment with a/the MAPK pathway inhibitor) once the melanoma acquires resistance to a MAPK pathway inhibitor results in better and improved treatment of MAPK pathway inhibitor resistant melanomas. The response of the melanoma to the sequential treatment (i.e. the xTCi or the combination of xTCi and HDACi is/are not or cannot be jointly/at the same time therapeutically active in the patient with the MAPK pathway inhibitor) is better than with simultaneous treatment with a MAPK pathway inhibitor and a xTCi (or xTCi and HDACi) (i.e. the case wherein the xTCi and the MAPK pathway inhibitor are jointly therapeutically active in the patient), the latter combination showing antagonistic effects resulting in a limited anti-cancer effect. In other words, after the treatment with the MAPK pathway inhibitor is discontinued, treatment with the xTCi (or xTCi and HDACi) is started, meaning that therapeutically acceptable amounts of an xTC inhibitor (or xTCi and HDACi) are provided to the patient (in other words, the patient is provided with an amount of at least one compound with the purpose of inhibiting the activity of XTC (and/or histone deacetylase in case also a HDACi is provided) in the patient with the aim of inducing or contributing to inducing a therapeutic effect). As a consequence of the discontinued treatment with the MAPK pathway inhibitor, the xTCi and the MAPK pathway inhibitor will no longer interact in the patient (i.e. the xTCi and the MAPK pathway inhibitor are not jointly therapeutically active in the patient), therewith preventing the antagonist effect of the combination observed by the current inventors. The XTCi, in absence of the MAPK pathway inhibitor was found to provide for effective and durable anti-cancer effects in the BRAF and/or NRAS mutilation harboring melanoma that acquired resistance to the MAPK pathway inhibitor or that are resistant to a MAPK pathway inhibitor.

Indeed a further surprising finding is that treatment with a HDACi in combination with a XCTi (i.e. treatment is performed in a manner so that the HDACi and XCTi are jointly therapeutically effective in the patient) works better (i.e. caused cell death or decreased cell survival) in melanoma harboring a BRAF-mutation or in melanoma harboring a NRAS-mutation (and that acquired resistance to a MAPK pathway inhibitor or that are resistant to a MAPK pathway inhibitor) than individual treatment with HDACi or XCTi. In other words, it appears the HDACi and XCTi work together in synergy to produce greater effects on the melanoma cells, as disclosed herein (i.e. cause greater cell death or reduce survival to a greater extent).

DRAWINGS

Figure 1A:
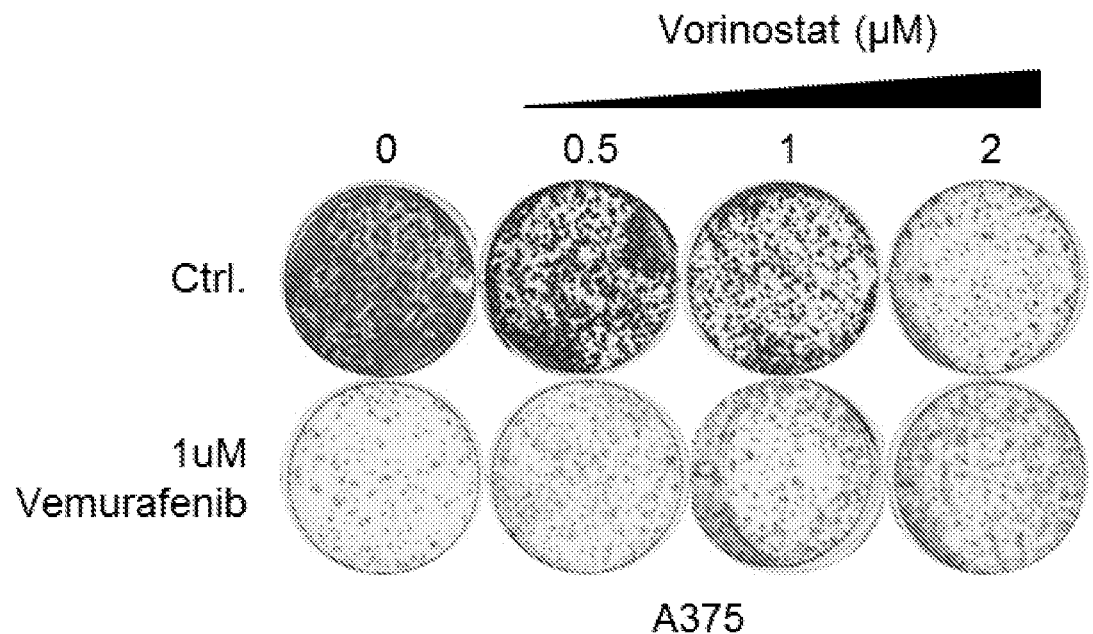
Figure 1B:
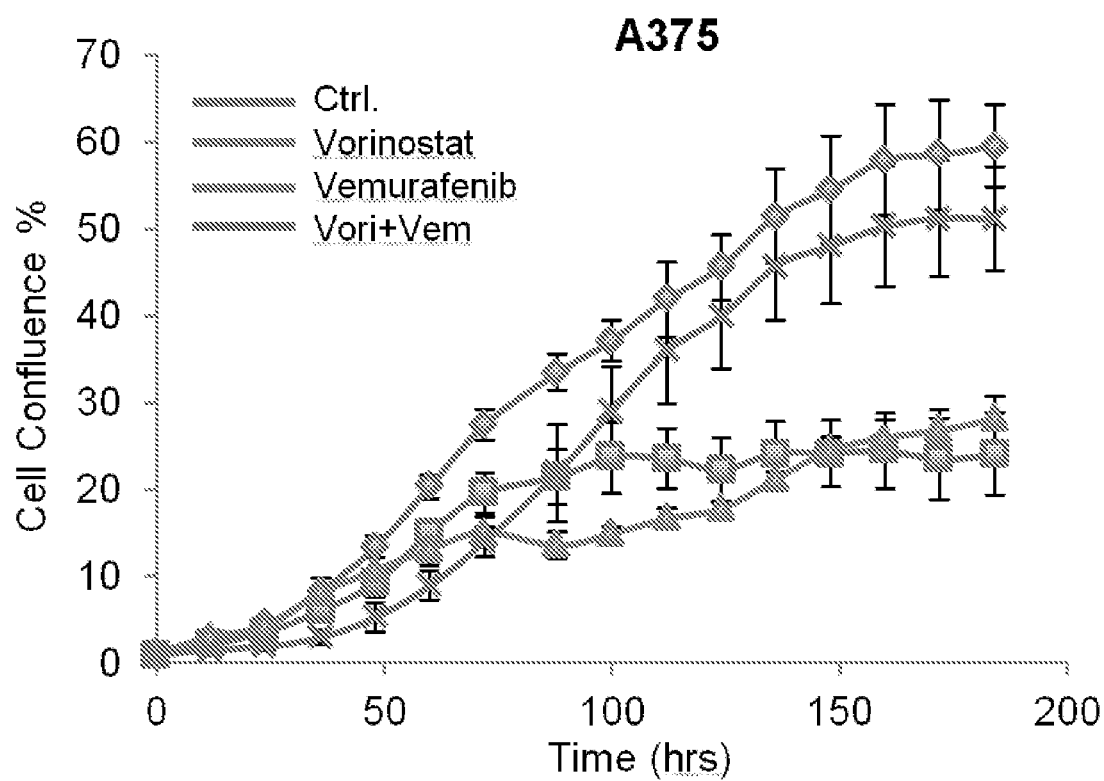
Figure 1D:
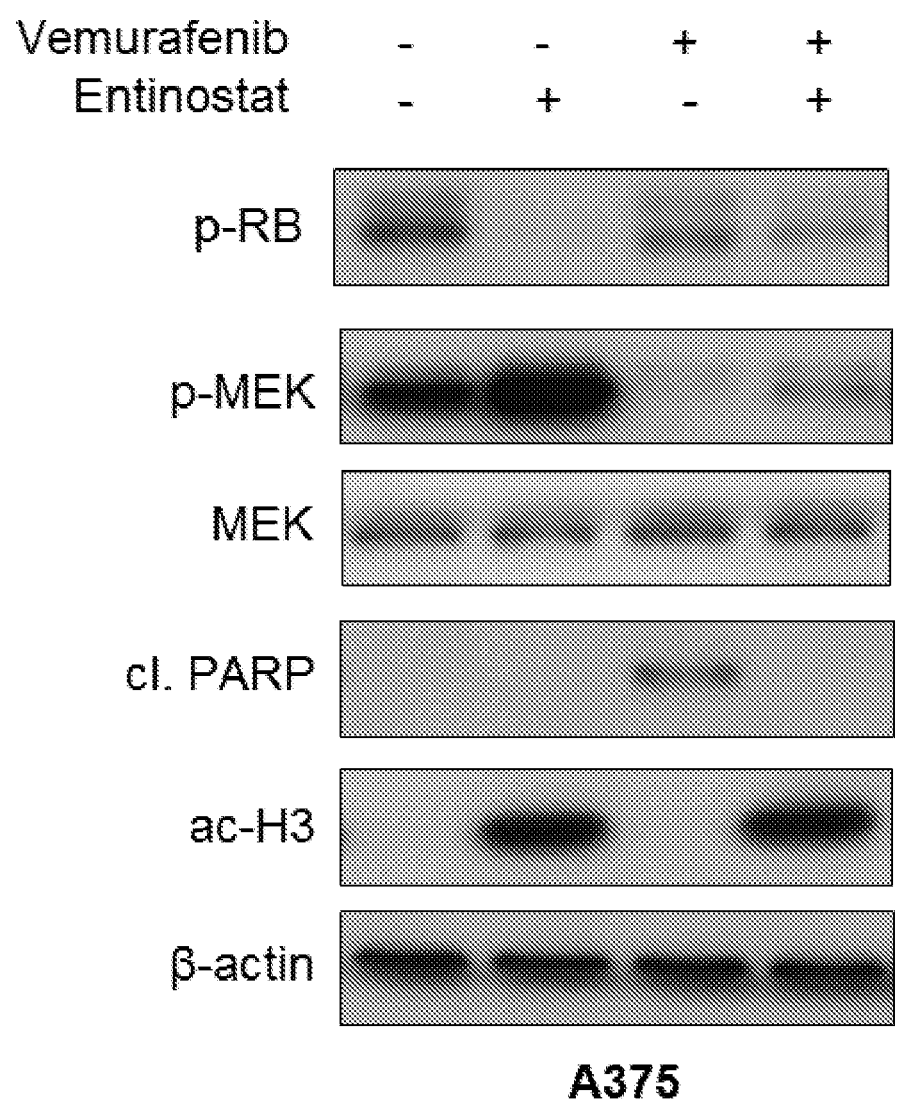

FIG. 1. BRAF inhibition is antagonized by HDAC inhibition in melanoma. A). Long-term colony formation assay of melanoma (A375) cells. Cells were seeded at the same density in 6-well plates and cultured in presence of vorinostat and/or vemurafenib at the indicated concentrations. The cells were fixed and stained at day 14. B). Short-term proliferation assay of melanoma (A375) cells. Cells were seeded in 384-well and cultured in presence of vorinostat (1 microM) and/or vemurafenib (1 microM) and cell confluence was measured by IncuCyte imaging. Error bars represent s.d. of biological triplicates. C,D). HDAC inhibitors and vemurafenib have antagonistic effects on MAPK pathway and HDAC inhibitors can rescue cells from vemurafenib-induced apoptosis. A375 were pre-treated with 1 microM vorinostat and 1 microM entinostat for 48 hrs and then treated with the combination of HDAC inhibitor (1 microM) and vemurafenib (1 microM) for additional 24 hrs. The levels of p-RB, p-MEK, MEK, cleaved PARP (cl. PARP) and ac-H3 were detected by western blot. $\beta$-actin served as the loading control.

FIG. 2. Other HDACi also confer resistance to vemurafenib. A) Long-term colony formation assay of melanoma (A375) cells seeded at the same density in 12-well plates and cultured in presence of several HDAC inhibitors (Panobinostat, Belinostat or CXD101) and/or vemurafenib at the indicated concentrations. Cells were fixed and stained at day 10. B). Colo741 cells were seeded at the same density in 6-well plates and cultured in presence of vorinostat and/or vemurafenib at the indicated concentration. Cells were fixed and stained at day 12.

Figure 3A:
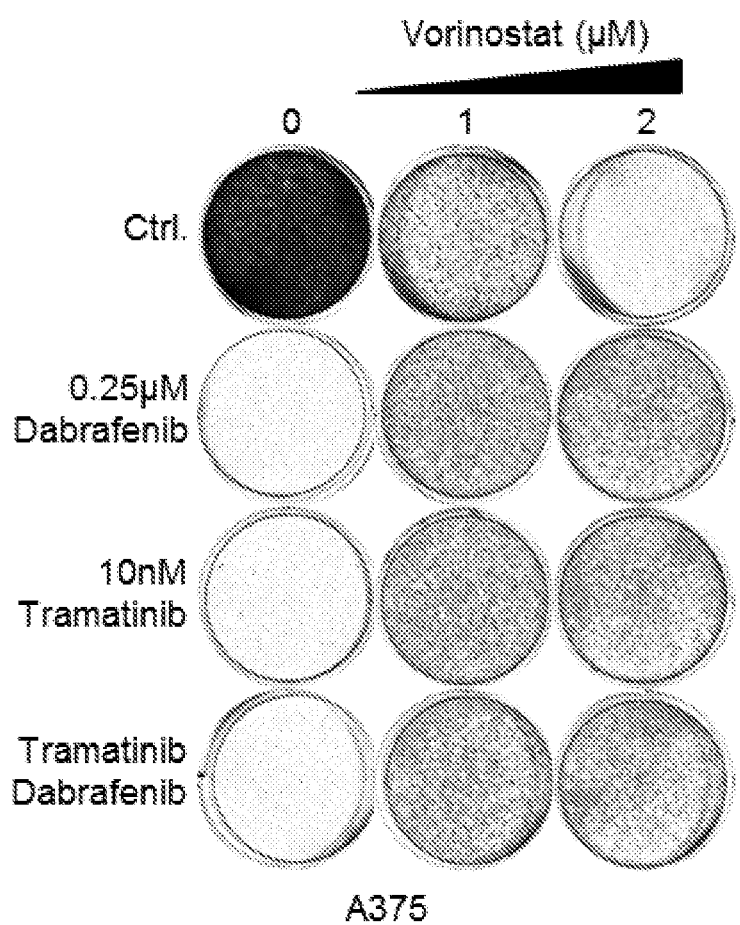
Figure 3B:
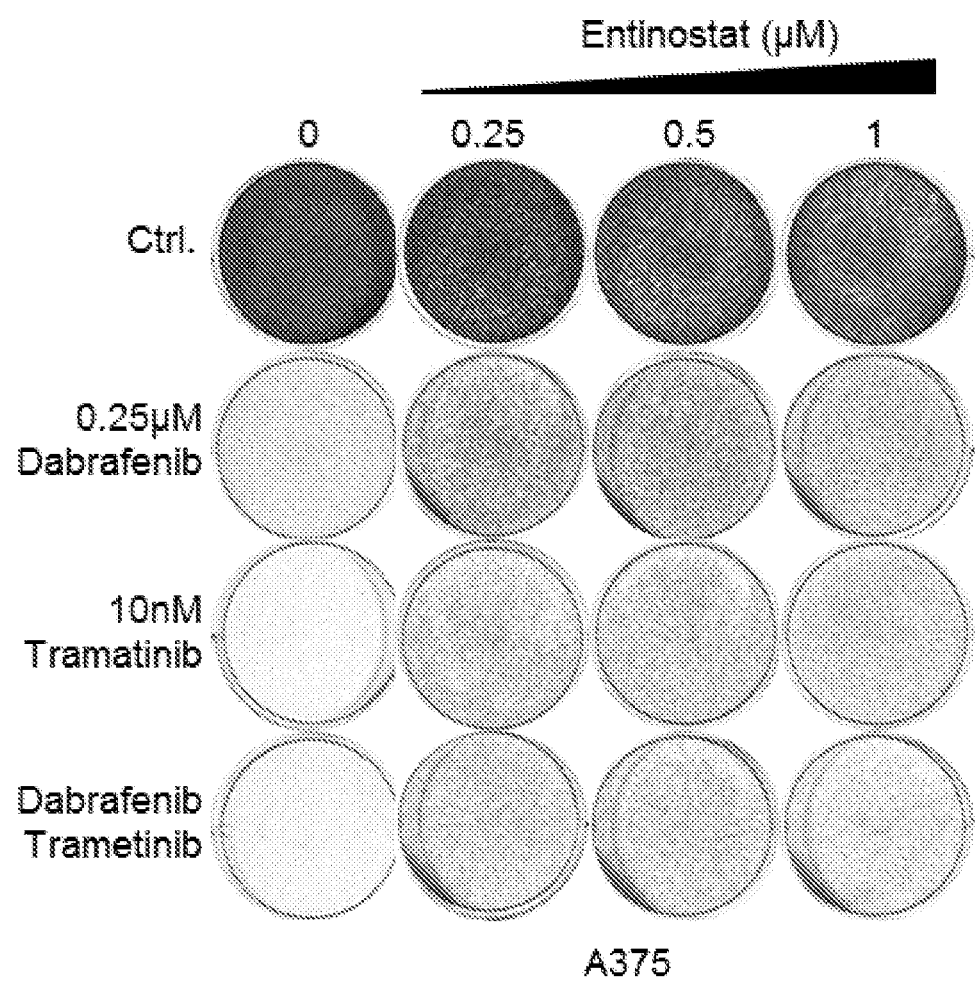
Figure 3C:
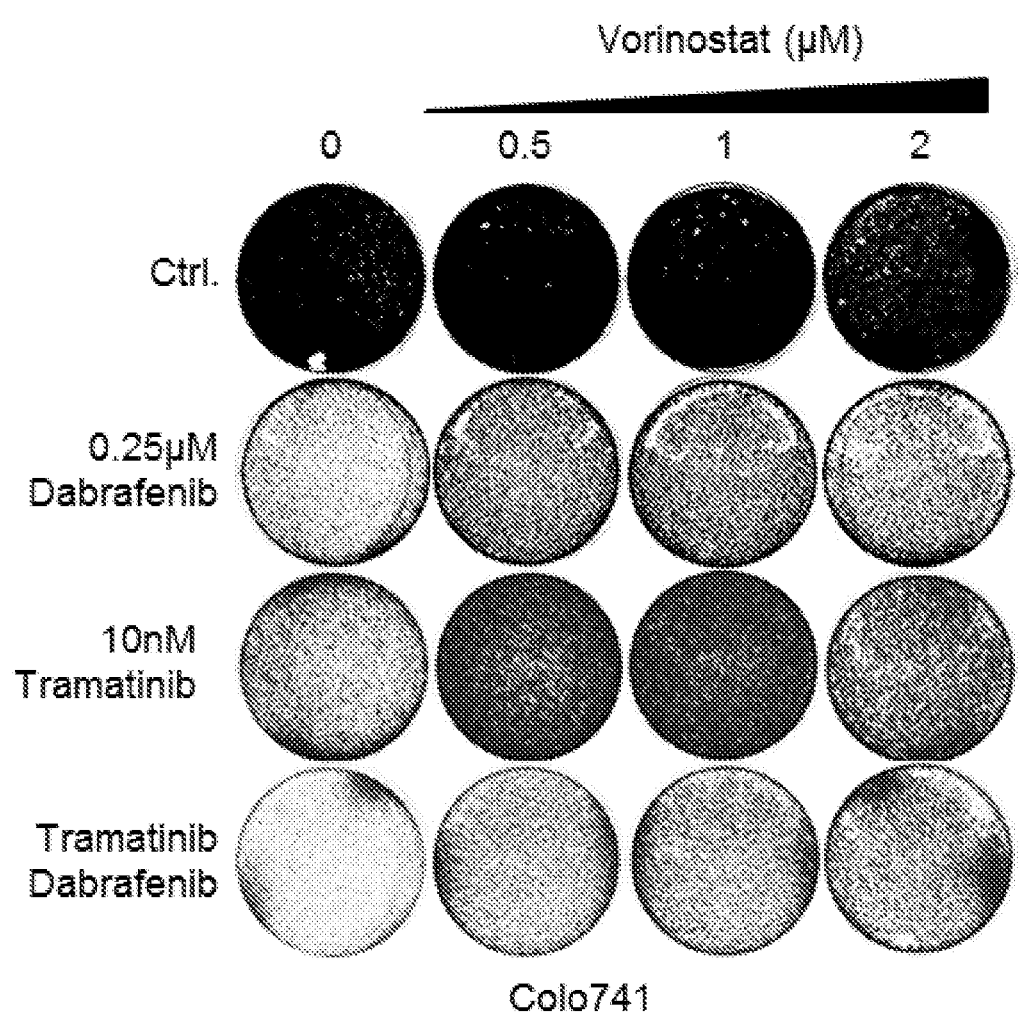

FIG. 3. HDACi confers resistance to the combination of a MEK and a BRAF inhibitor in melanoma. A,B,C). Long-term colony formation assay of melanoma (A375 and Colo741) cells seeded at the same density in 6-well plates and cultured in presence of increasing concentrations of HDAC inhibitors (vorinostat/entinostat) and/or BRAF inhibitor (dabrafenib) and MEK inhibitor (trametinib) or their combination at the indicated concentration. Cells were fixed and stained at day 10.

FIG. 4. HDACi treatment is detrimental for BRAF inhibitor resistant melanoma. A). Long-term colony formation assay of melanoma (A375 and A375R clone) cells. Vemurafenib-resistant A375R cells are hypersensitive to vorinostat mono-treatment. A375 and A375R cells were seeded at the same cell density in 6-well plates and in presence of vorinostat (1 microM) and/or vemurafenib (2 microM). Cells were fixed and stained at day 12. B). Vemurafenib-resistant A375R cells hyperactivate the MAP kinase pathway. The levels of PDGFRB, p-SHP2, p-MEK, MEK, p-ERK, ERK, p-AKT and AKT were detected by western blot. HSP90 served as the loading control. C). Vemurafenib-resistant Mel888R cells are hypersensitive to vorinostat treatment. Long-term colony formation assay of melanoma Mel888 parental and vemurafenib-resistant Mel888R cells (three different clones Mel888RC-A, B and C) were seeded at the same cell density in 6-well plates and cultured in presence of vorinostat (1 microM) and/or vemurafenib (2 microM). Cells were fixed and stained at day 10. D). Dabrafenib/trametinib double-resistant A375DR cells are hypersensitive to CDX101. Long-term colony formation assay of melanoma A375 parental and double-resistant cells seeded in 12-well plates and treated with 2 microM vemurafenib and/or 0.5 microM CDX101 (CDX). Medium and drugs were refreshed every 2-3 days. Cells were fixed and stained on day 10.

Figure 5:
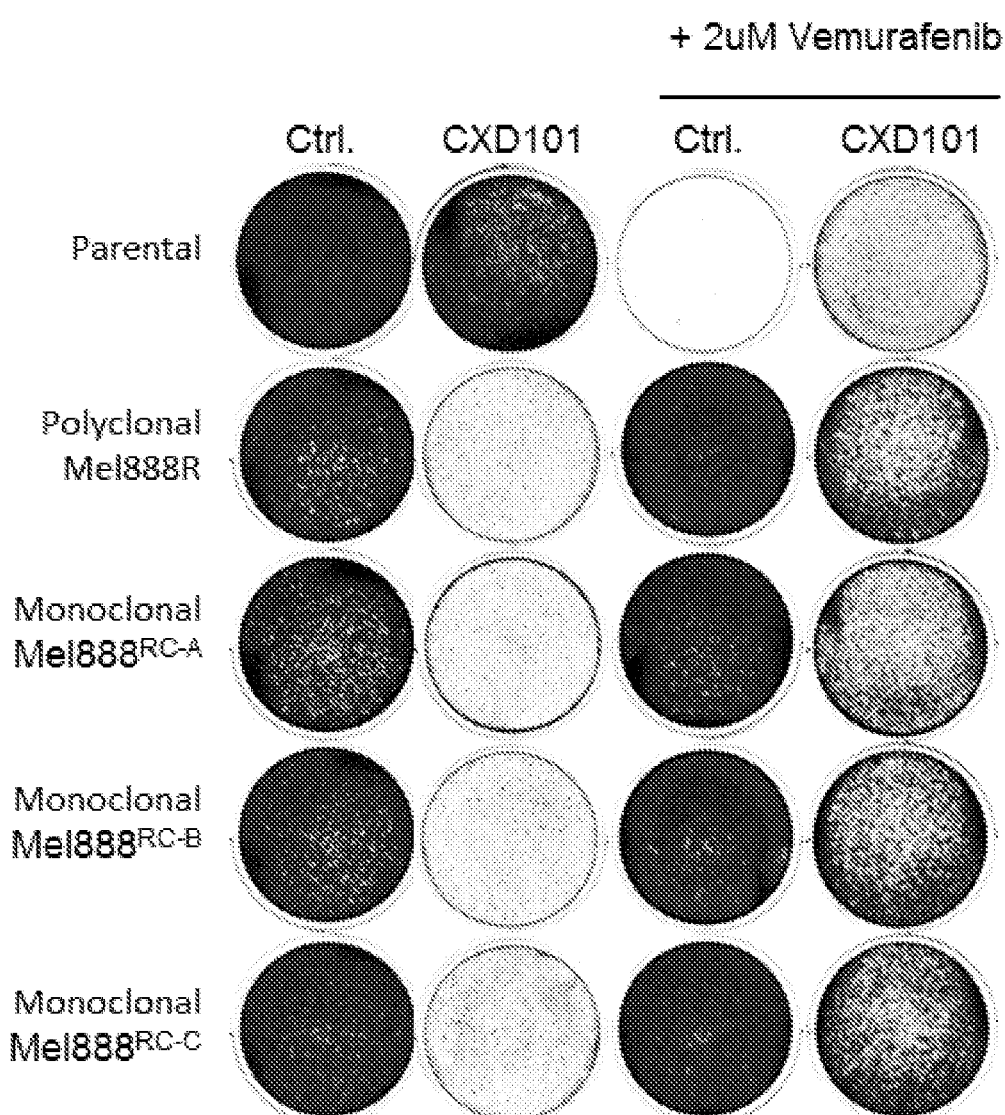

FIG. 5. Vemurafenib-resistant Mel888R cells are hypersensitive to CDX101. Long-term colony formation assay of melanoma Mel888 parental and several resistant clones seeded in 12-well plates and treated with 2 microM vemurafenib and/or different HDAC inhibitors, 1 microM Vorinostat (Vor), 0.5 microM CXD101 (CXD). Medium and drugs were refreshed every 2-3 days. Cells were fixed and stained on day 8.

Figure 6:
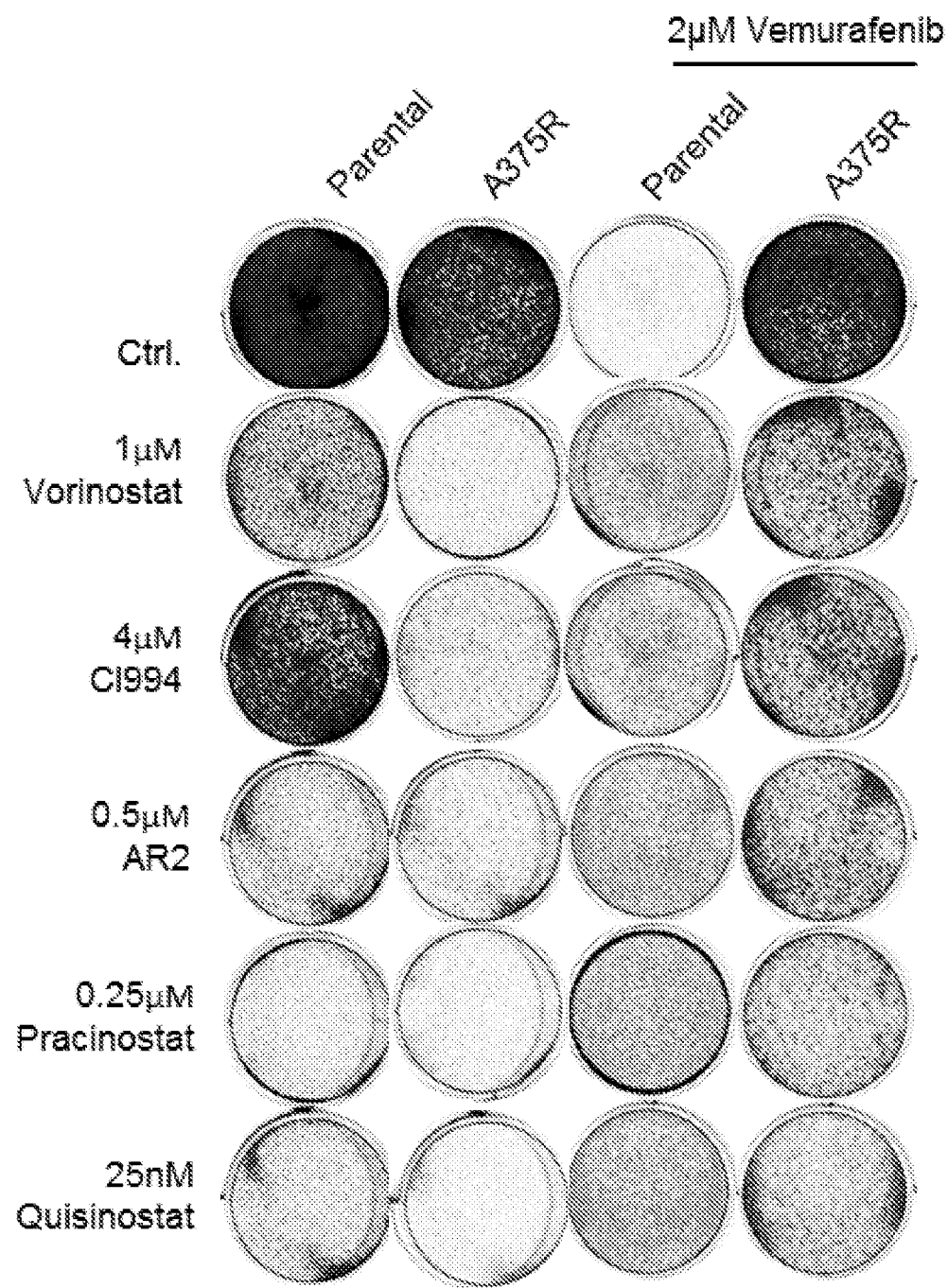

FIG. 6. BRAF inhibitor resistant melanoma is sensitive to a panel of HDAC inhibitors. Long-term colony formation assay of melanoma A375 parental and A375R cells seeded in 12-well plates and treated with 2 microM vemurafenib and/or a panel of five different HDAC inhibitors with the indicated concentrations. Medium and drugs were refreshed every 2-3 days. Cells were fixed and stained on day 10

FIG. 7. HDACi is effective in treatment of BRAF inhibitor resistant melanoma in vivo. A,B). Sequential treatment with vemurafenib and vorinostat suppress melanoma growth in a xenograft model. A375 melanoma cells were grown as tumor xenografts in BalbC immunodeficient nude mice. After tumor establishment (150-200 mm3), mice were treated with (A). vehicle, PLX4720 (40 mg/kg supplemented in the chow). Upon development of BRAF inhibitor resistance, mice receiving PLX4720 were randomized in four arms (B) receiving: vehicle, PLX4720 (300 mg/kg supplemented in the chow), Vorinostat (100 mg/kg i.p.) or PLX4720 (300 mg/kg supplemented in the chow) plus Vorinostat (100 mg/kg i.p.). C). Resistance to vemurafenib in A375 cells is mediated through reactivation of MAP kinase pathway. Biochemical responses of A375-resistant ex vivo clones and A375 parental cell line treated with 2 microM vemurafenib were documented by western blot analysis. Cells were harvested at 24 hrs after drug treatment. The levels of PDGFRB, p-SHP2, p-MEK, MEK, P-ERK, ERK, p-AKT and AKT were detected by western blot. BRAF inhibition in the parental line results in loss of p-MEK, which is abrogated in all resistant clones. HSP90 served as the loading control. HSP90 served as a control.

Figure 8:
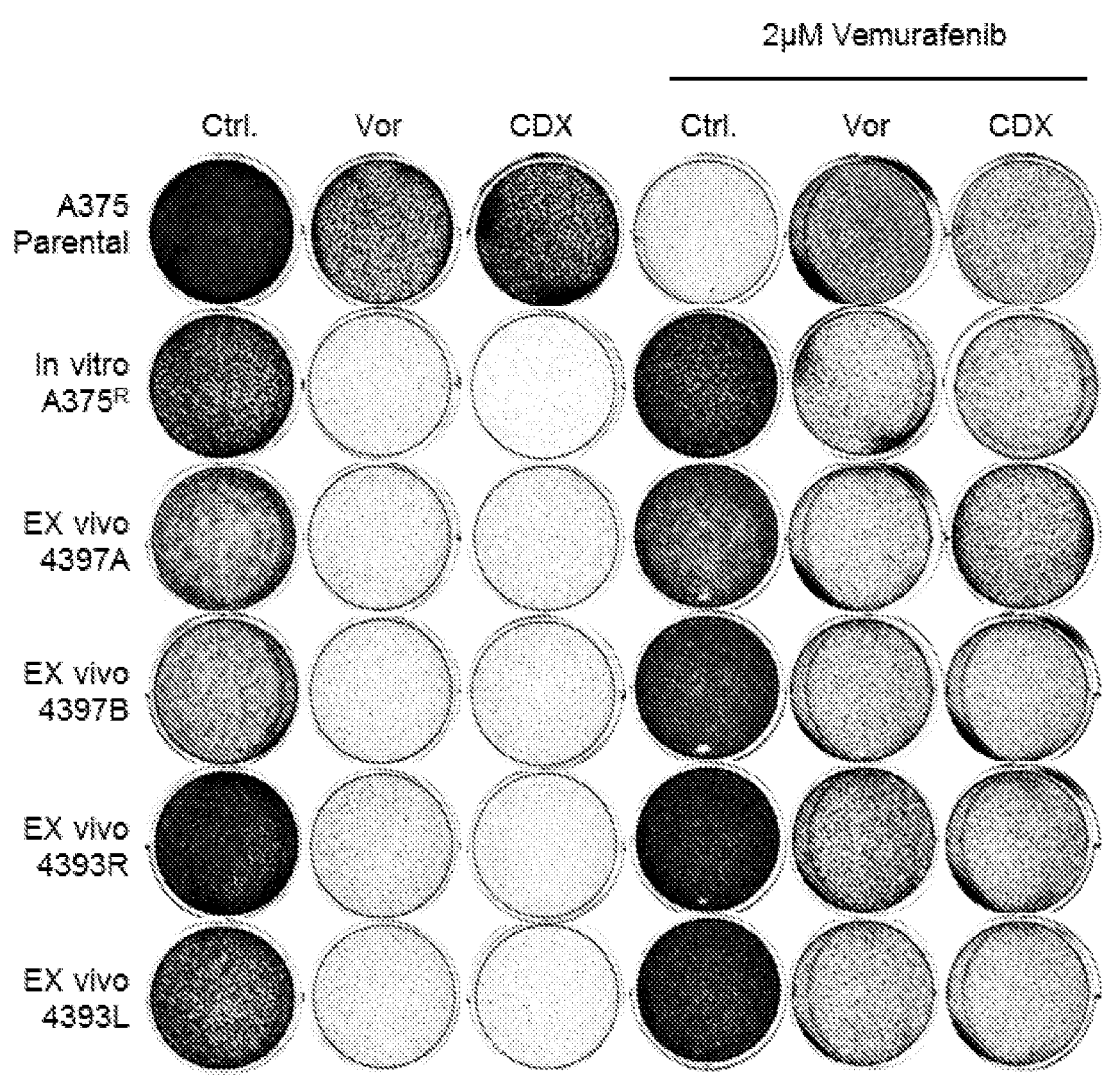

FIG. 8. In vitro and ex vivo BRAF inhibitor-resistant clones are hypersensitive to HDACi. Long-term colony formation assay of melanoma A375 parental and A375 in vitro and ex vivo resistant cells seeded in 12-well plate and treated with 2 microM vemurafenib and/or different HDAC inhibitors, 1 microM Vorinostat (Vor), 0.5 microM CDX101. Medium and drugs were refreshed every 2-3 days. Cells were fixed and stained on day 10.

FIG. 9. MEK inhibitor resistant NRAS mutant melanomas are sensitive to HDACi.

(a). Long-term colony formation assay of SK-MEL-147 and MEKi-resistant SK-MEL-147R cells cultured in the presence of 1 μM vorinostat and/or 100 nM Trametinib. Medium and drugs were refreshed every 2-3 days. Cells were fixed and stained on day 10.

(b). Long-term colony formation assay of SK-MEL-147 and SK-MEL-147R cells cultured in the presence of indicated concentrations of vorinostat and/or 5 mM NAC. Medium and drugs were refreshed every 2-3 days. Cells were fixed and stained on day 10.

(c). Additional BRAF(V600E) mutation in SK-MEL0147R was identified by Sanger sequencing analysis.

(d). HDAC inhibitor suppressed SLC7A11 expression in SK-MEL-147 parental and SK-MEL-147R cells. The relative mRNA levels were detected by qRT-PCR analysis after 72 hours vorinostat treatment. Error bars represent s.d. of measurement replicates (n=3, *** p<0.001, Student's t-test).

(e). Basal levels of ROS (CellROX Green fluorescent signal) are higher in SK-MEL-147R cells compared to parental cells and increase further by 72 hours of vorinostat treatment. NAC (N-acetyl-L-cysteine) was used as a ROS scavenger control. Error bars represent s.d. of biological triplicates (n=3, * p<0.001,  p<0.005, * p<0.05, Student's t-test).

(f). Ectopic expression of SLC7A11 rescued SK-MEL-147 parental and SK-MEL-147R cells from HDAC inhibition. SLC7A11 expression vector was introduced into the cells by lentiviral transduction. Empty vector served as a control. After blasticidin selection, cells were seeded in 6-well plate for a long-term colony formation assay and treated with 1 μM vorinostat. Empty vector served as a control. Medium and drugs were refreshed every 2-3 days. Cells were fixed and stained on day 8.

(g). Relative induction of SLC7A11 expression in lentiviral induced SK-MEL-147 parental and SK-MEL-147R cells. Empty vector served as a control. Error bars represent s.d. of biological triplicates (n=3, *** p<0.001, Student's t-test).

(h). Ectopic expression of SLC7A11 reduced the ROS levels that were induced by HDAC inhibition in SK-MEL-147 parental and SK-MEL-147R cells. The relative ROS levels (CellROX Green fluorescent signal) were detected using flow cytometry after 72 hours vorinostat treatment. Error bars represent s.d. of biological triplicates (n=3, ** p<0.005, * p<0.05, Student's t-test).

(i). Long-term colony formation assay of SK-MEL-2 and MEKi-resistant SK-MEL-2R cells cultured in the presence of 1 μM vorinostat and/or 100 nM Trametinib. Medium and drugs were refreshed every 2-3 days. Cells were fixed and stained on day 10.

(j) Long-term colony formation assay of SK-MEL-2 and SK-MEL-2R cells cultured in the presence of indicated concentrations of vorinostat and/or 5 mM NAC. Medium and drugs were refreshed every 2-3 days. Cells were fixed and stained on day 10.

FIG. 10. HDAC inhibitors modulate SLC7A11 to increase ROS levels in melanoma.

(a). HDAC inhibitor suppressed SLC7A11 expression in A375 parental, A375R and A375DR cells. The relative mRNA levels were detected by qRT-PCR analysis after 72 hours vorinostat treatment. Error bars represent s.d. of measurement replicates (n=3, *** p<0.001, Student's t-test).

(b). Knockdown efficiency of 4 independent shRNAs targeting SLC7A11 in A375 parental cells. The relative mRNA levels were detected by qRT-PCR analysis. Error bars represent s.d. of measurement replicates (n=3, *** p<0.001, Student's t-test).

(c). Suppression of SLC7A11 using shRNAs leaded to ROS induction in A375 parental cells. The relative ROS levels (CellROX Green fluorescent signal) were detected using flow cytometry. NAC was used as a ROS scavenger control.

(d). Long-term colony formation assay of A375 parental, A375R and A375DR cells treated with independent shRNAs targeting SLC7A11. pLKO.1 empty vector served as a control. Medium and drugs were refreshed every 2-3 days. Cells were fixed and stained on day 8.

(e). Ectopic expression of SLC7A11 rescued A375R and A375DR cells from HDAC inhibition. SLC7A11 expression vector was introduced into the cells by lentiviral transduction. Empty vector served as a control. After blasticidin selection, cells were seeded in 96-well plate and treated with 1 μM vorinostat. Cell confluence was measured by IncuCyte imaging system. Error bars represent s.d. of biological triplicates (n=3, *** p<0.001, Student's t-test).

(f). Long-term colony formation assay of A375 parental, A375R and A375DR cells lentiviral transduced with SLC7A11 expressing vector and treated with 1 μM vorinostat. Empty vector served as a control. Medium and drugs were refreshed every 2-3 days. Cells were fixed and stained on day 10.

(g). Relative induction of SLC7A11 expression in lentiviral induced A375, A375R and A375DR cells. Empty vector served as a control. Error bars represent s.d. of biological triplicates (n=3, *** p<0.001, Student's t-test).

(h). Ectopic expression of SLC7A11 reduced the ROS levels that were induced by HDAC inhibition in A375, A375R and A375DR cells. The relative ROS levels (CellROX Green fluorescent signal) were detected using flow cytometry after 72 hours vorinostat treatment. Error bars represent s.d. of biological triplicates (n=3, *** p<0.001, Student's t-test).

Figure 11:
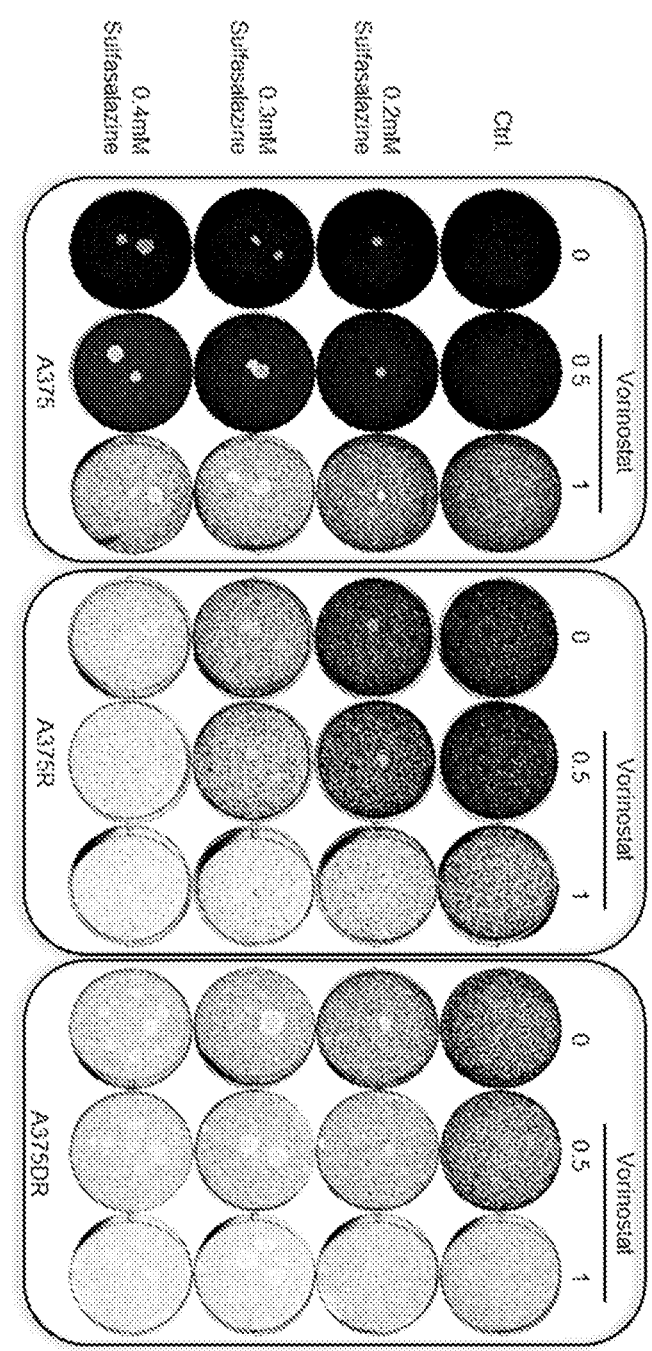

FIG. 11. SLC7A11 inhibition is synergistic with HDAC inhibition in BRAF inhibitor resistant melanoma. Long-term colony formation assay of A375 parental and MAPKi resistant A375R, A375DR cells treated sulfasalazine and vorinostat. Medium and drugs were refreshed every 2-3 days. Cells were fixed and stained on day 10.

DEFINITIONS

Various terms relating to the methods, compositions, uses and other aspects of the present invention are used throughout the specification and claims. Such terms are to be given their ordinary meaning in the art to which the invention pertains, unless otherwise indicated. Other specifically defined terms are to be construed in a manner consistent with the definition provided herein. Although any methods and materials similar or equivalent to those described herein can be used in the practice for testing of the present invention, the preferred materials and methods are described herein.

The amino acid sequence of (human) BRAF, NRAS, RAF, ERK, MEK, RAS, RSK or any other (human) protein mentioned herein, and variations thereof are available in GenBank, accessible via www.ncbi.nlm.nih.gov/genbank.

As used herein, the singular forms "a," "an" and "the" include plural referents unless the context clearly dictates otherwise. For example, a method for administrating a drug includes the administrating of a plurality of molecules (e.g. 10's, 100's, 1000's, 10's of thousands, 100's of thousands, millions, or more molecules).

As used herein, the term "and/or" indicates that one or more of the stated cases may occur, alone or in combination with at least one of the stated cases, up to with all of the stated cases.

As used herein, "to comprise" and its conjugations is used in its non-limiting sense to mean that items following the word are included, but items not specifically mentioned are not excluded. It also encompasses the more limiting "to consist of".

As used herein, with "an effective amount" is meant the amount of a drug required to ameliorate the symptoms of a disease relative to an untreated patient. The effective amount of active agent(s) used to practice the present disclosure for therapeutic treatment of melanoma varies depending upon the manner of administration, the age, body weight, and general health of the subject. Ultimately, the attending physician will decide the appropriate amounts and dosage regimen. Such amount is referred to as an "effective" or "acceptable" amount. Thus, in connection with the administration of a drug which, in the context of the current disclosure, is "effective against" a disease or condition indicates that administration in a clinically appropriate manner results in a beneficial effect for at least a statistically significant fraction of patients, such as an improvement of symptoms, a cure, a reduction in at least one disease sign or symptom, extension of life, improvement in quality of life, or other effect generally recognized as positive by medical doctors familiar with treating the particular type of disease or condition.

As used herein, in general the term "inhibitor" of a (defined) protein or enzyme, for example ERK, refers to any compound capable of down-regulating, decreasing, suppressing or otherwise regulating the amount and/or activity of the (defined) protein, for example ERK, for example, to a level of 50%, 30%, 20% or 10% or less compared to the control (without the presence of such inhibitor). Inhibitors may include, but are not limited to small molecules (chemical compound having a molecular weight below 2,500 daltons, more preferably between 300 and 1,500 daltons, and still more preferably between 400 and 1000 daltons), antibodies directed to the particular protein or enzyme, compounds that down-regulate gene expression, translation and/or transcription, including such RNA molecules capable of RNA interference including, without limitation, siRNA, shRNA, and miRNA. The inhibitors to be used in accordance with the present invention may be selective inhibitors of said (defined) protein, as already described above; the term "selective" or "selectivity" expresses the biologic fact that at a given compound concentration enzymes (or proteins) are affected to different degrees. In the case of proteins selective inhibition can be defined as preferred inhibition by a compound at a given concentration. In other words, an enzyme is selectively inhibited over another enzyme when there is a concentration which results in inhibition of the first enzyme whereas the second enzyme is not affected. To compare compound effects on different enzymes it is important to employ similar assay formats. For the proteins/enzymes as disclosed herein, such assay formats are readily available in the prior art.

The term "subject" or "patient" as used herein includes animals, which are capable of suffering from melanoma, in particular BRAF and/or NRAS mutation harboring melanoma. Examples of subjects include mammals, e.g., humans, dogs, mice, rabbits, rats and transgenic non-human animals. In a preferred embodiment, the subject is a human suffering from melanoma, in particular suffering from a BRAF-mutated and/or NRAS mutated melanoma. In some disclosures, and in a more preferred embodiment, the BRAF-mutated and/or NRAS mutated melanoma, preferably in a human, has acquired resistance to treatment with a MAPK pathway inhibitor.

The term "therapeutically acceptable amount" or "clinically effective amount" or is an amount of a drug sufficient to provide an observable improvement over the baseline clinically observable signs and symptoms of the disorder treated with the drug.

The term "treatment" or "treating" as used herein comprises a treatment relieving, reducing or alleviating at least one symptom in a subject or effecting a delay of progression of a disease. Within the meaning of the present invention, the term "treat" also denotes to arrest, delay the onset (i.e., the period prior to clinical manifestation of a disease) and/or reduce the risk of developing or worsening a disease.

The term "pharmaceutically acceptable" as used herein refers to those compounds, materials, compositions and/or dosage forms, which are, within the scope of sound medical judgment, suitable for administration to a subject or suitable for contact with the tissues a subject, e.g., a mammal or human, without excessive toxicity, irritation allergic response and other problem complications commensurate with a reasonable benefit/risk ratio.

The term "not jointly therapeutically active" as used herein means that the therapeutic agents, e.g. HDACi and MAKP pathway inhibitor, are given separately (in a chronologically staggered manner, especially a sequence-specific manner, e.g. the MAKP pathway inhibitor agent is given first and the HDACi agent is given second after the MAKP pathway inhibitor is discontinued) in such time intervals that they do not show an interaction (e.g. no joint therapeutic effects between the HDACi and MAKP pathway inhibitor) in the subject receiving the treatment with said agent. Whether this is the case can, inter alia, be determined by following the blood levels, showing that both compounds (e.g. HDACi and MAKP pathway inhibitor) are not present at the same time in the blood of a subject receiving the treatment with said compounds.

The term "co-administration" or "combined administration" as used herein is defined to encompass the administration of the selected therapeutic agents (e.g. HDACi and XCTi, as taught herein) to a single patient, and are intended to include treatment regimens in which said agents are not necessarily administered by the same route of administration or at the same time but are administered in a manner so that said agents are jointly therapeutically active in said patient, for a given period of time.

DETAILED DESCRIPTION

The present invention relates in a first aspect to a histone deacetylase inhibitor (HDACi) for use in the treatment of a subject with melanoma characterized in that the melanoma is a BRAF-mutation or a NRAS-mutation harboring melanoma that has acquired resistance to a mitogen-activated protein kinase (MAPK) pathway inhibitor (or more than one) and wherein the treatment with the HDACi does not involve the simultaneous treatment with a MAPK pathway inhibitor.

Reversible acetylation of histones is a major regulator of gene expression that acts by altering accessibility of transcription factors to DNA. In normal cells, histone deacetylase (HDAC) and histone acetyltransferase together control the level of acetylation of histones to maintain a balance. Inhibition of HDAC results in the accumulation of hyperacetylated histones, which results in a variety of cellular responses. HDACi have been studied for their therapeutic effects on cancer cells. Recent developments in the field of HDACi research have provided active compounds, both highly efficacious and stable, that are suitable for treating cancer. Histone deacetylase inhibitors (HDAC inhibitors, HDACi) are known to the skilled person as a class of compounds that interfere with the function of histone deacetylases, as explained above. Any suitable HDACi may be used in the methods of the present invention. Non-limiting examples of HDACi's useful in the current invention include vorinostat, CXD-101, entinostat, 01994, AR42, practinostat, quisinostat, panobinostat (PXD101), belinostat and romidepsin. Other useful HDACi include trichostatin A, Chidamide (Epidaza), Mocetinostat (MGCD0103), Abexinostat (PCI-24781), Entinostat (MS-275), SB939, Resminostat (4SC-201), Givinostat (ITF2357), Kevetrin, CUDC-101, CHR-2845, CHR-3996, ME-344, BL-1521, PX-118490, ONO-4817, Tosedostat, Pyroxamide, Batimastat, Tefmostat, tefinostat, and Bufexamac. For instance, panobinostat may be a useful HDACi for use in the present invention. Panobinostat has the chemical name N-hydroxy-3-[4-[[[2-(2-methyl-1H-indol-3-yl)-ethyl]-amino]methyl]phenyl]-2£-2-propenamide, and is disclosed in published PCT patent application WO02/22577, which is hereby incorporated by reference in its entirety. These and other HDACi are known to the skilled person.

Histone deacetylase (HDAC) inhibitors are emerging as a promising class of compounds in the treatment of cancer with low in vivo side-effect profiles, although monotherapy with HDAC inhibitors may not be superior to, for example, dacarbazine (DTIC) in the treatment of melanoma. Cell death by HDAC inhibitors may involve regulation of various Bcl-2 family proteins including Bim and Mcl-1. Furthermore, HDAC inhibitors such as suberoylanilide hydroxamic acid (SAHA) can also induce caspase-independent cell death.

The skilled person, e.g. a medical doctor or medical or health practitioner treating cancer patients, possesses deep or advanced knowledge of compounds medically or clinically or pharmaceutically indicated for the purpose of treating cancer, including HDACi compounds as taught herein and others. In the context of the present invention, HDACi compounds are chosen on the basis that they are medically or clinically, or pharmaceutically indicated for the purpose of treating cancer, e.g. melanoma.

Preferably the HDACi is a selective HDACi, meaning it inhibits histone deacetylase while, under comparable conditions, not or only to a limited extent inhibiting MAPK pathway (i.e. while only inhibiting RAS, RAF, MEK, ERK and/or RSK to a limited extend). Preferably the HDACi is approved for use in humans. Preferably the HDACi is a pharmaceutically or clinically acceptable HDACi suitable for the treatment of cancer.

In the invention the subject is treated with a therapeutically acceptable amount of the HDAC inhibitor. The skilled person will understand that the exact amount depends on, for example, the HDACi used, the individual treated and the mode of administration. A suitable dosage or dosage regimen may be determined by the skilled person using routine experimentation. The optimal dosage can be determined empirically using known methods and will depend upon a variety of factors, including, though not limited to, the degree of advancement of the disease; the age, body weight, general health, gender and diet of the individual; the time and route of administration; and other medications the individual is taking.

In some embodiment more than one HDACi may be used, for example combined or alternated.

Within the context of the current invention, the HDACi is used in the treatment of a subject, the subject preferably being a human having a melanoma.

Melanoma are very well-known to the skilled person and are also known as malignant melanoma (see, for example, www.cancer.gov/types/skin/hp/melanoma-treatment-pdq).

In some embodiments, the melanoma is a BRAF-mutation and/or a NRAS-mutation harboring melanoma.

In a preferred embodiment, the melanoma is a BRAF-mutated melanoma, i.e. a melanoma harboring mutation in BRAF. The term "BRAF-mutated cancer" or "BRAF-mutation harboring melanoma" is well known to the skilled person. BRAF (e.g. Gene accession number 673; Refseq RNA Accessions NM_004333.4; protein NP_004324.2), is a member of the RAF family, which includes ARAF and CRAF in humans (Ikawa, Mol Cell Biol. 8(6):2651-4 (1988)). BRAF is a serine/threonine protein kinase and participates in the RAS/RAF/MEK/ERK/RSK mitogen activated protein kinase pathway (MAPK pathway, see Williams & Roberts, Cancer Metastasis Rev. 13(1):105-16 (1994); Fecher et al 2008 Curr Opin Oncol 20, 183-189 or Cargnello M, Roux P P. Microbiol Mol Biol Rev. 2011 March; 75(1):50-83). Approximately 40-60% of (cutaneous)

melanomas carry a mutation in the BRAF protein. Approximately 90% of these mutations result in the substitution of glutamic acid for valine at codon 600 (BRAF V600E), although other mutations are also known (e.g. BRAF V600K and BRAF V600R). Such mutation in BRAF typically leads to proliferation and survival of melanoma cells (Davies et al Nature 2002; 417:949-54; Curtin et al N Engl J Med 2005; 353:2135-47).

In a preferred embodiment, the melanoma is a NRAS-mutated cancer, i.e. a melanoma harboring NRAS-mutations. The term "NRAS-mutated melanoma" or "NRAS mutation harboring melanoma" is well known to the skilled person. A comprehensive overview of RAS mutations, including NRAS-mutations, in cancer was reported by Prior (Prior et al (2012) Cancer Res; 2457-67). NRAS-mutant cells promote ontogenesis due to being mutationally activated, in most cases, at codon 12, 13 and 61.

The NRAS protein is a GTPase enzyme that in humans is encoded by NRAS (neuroblastoma RAS viral (v-ras) oncogene homolog) gene (e.g. Gene accession number 4893; Refseq RNA Accessions NM_002524.4; protein NP_002515.1). The N-ras gene specifies two main transcripts of 2Kb and 4.3Kb, both transcripts appear to encode identical proteins as they differ only in the 3' untranslated region.

According to this aspect of the invention, the NRAS- and/or BRAF-mutation(s) harboring melanoma has, preferably, acquired resistance to a mitogen-activated protein kinase (MAPK) pathway inhibitor.

The MAPK pathway is well known to the skilled person and is sometime also referred to as the MAPK/ERK pathway, the RAS-RAF-MEK-ERK pathway, or the RAS-RAF-MEK-ERK-RSK pathway. The MAPK pathway, as used herein, is a chain or pathway of proteins in the cell that communicates a signal from a receptor on the surface of the cell to the DNA in the nucleus of the cell. In the MAPK pathway, activated RAS activates the protein kinase activity of RAF kinase, RAF kinase phosphorylates and activates MEK (MEK1 and MEK2), MEK phosphorylates and activates a mitogen-activated protein kinase (MAPK) ERK1 and ERK2 (MAPK3 and MAPK1). MAPK phosphorylates ribosomal protein S6 kinase (RPS6KA1; RSK).

Within the context of the current invention, a MAPK pathway inhibitor is a compound that inhibits signaling through the MAPK pathway, preferably by inhibiting the activity of one of the proteins forming the chain or pathway. Preferably the MAPK pathway inhibitor is an inhibitor of a protein of the MAPK pathway, including RSK, preferably an inhibitor of RAS, an inhibitor of RAF, an inhibitor of MEK, an inhibitor of ERK and/or an inhibitor of RSK. The skilled person, e.g. a medical doctor or medical or health practitioner treating cancer patients, possesses deep or advanced knowledge of compounds medically or clinically or pharmaceutically indicated for the purpose of treating cancer, including MAPK pathway inhibitors as taught herein and others. In the context of the present invention, MAPK pathway inhibitor compounds are medically or pharmaceutically indicated for the purpose of treating cancer, e.g. melanoma.

A RAS protein, polypeptide or peptide is to indicate a polypeptide belong to the RAS family, more in particular to as encoded by HRAS, KRAS, and NRAS in humans. The RAS protein is a GTP-binding protein having the function to transduce signals to MAPKKK as a RAF protein in the MAPK signaling pathway. The genes are the most common oncogenes in human cancer; mutations that permanently activate RAS are found in 20% to 25% of all human tumors. RAS inhibitors are being studied as a treatment for cancer, and other diseases with RAS overexpression. By RAS inhibitor is meant a compound that reduces the biological activity of RAS in the MAPK pathway; or that reduces the expression of an mRNA encoding a RAS polypeptide or that reduces the expression of a RAS polypeptide. RAS inhibitors are known to the skilled person. Any suitable RAS inhibitor clinically or pharmaceutically indicated for the treatment of cancer, e.g. melanoma, may be used in the present invention. Non-limitative examples of RAS inhibitors include the compounds trans-farnesylthiosalicylic acid (FTS, Salirasib), R115777 (Zarnesta), BMS-214662, SCH66336, L-778, and FTI-277.

A RAF protein, polypeptide or peptide is to indicate a polypeptide having serine/threonine protein kinase activity belonging to the RAF kinase family. RAF kinases are a family of three serine/threonine-specific protein kinases that are related to retroviral oncogenes. The three RAF kinase family members are ARAF (A-RAF; for example Genbank Accession NO: NP001243125), BRAF (B-RAF; (for example, Genbank Accession NO: NP004324)) and CRAF (C-RAF; (e.g. Gene accession number 5894; Refseq RNA Accessions NM_002880.3; protein NP_002871.1), and well-known to the skilled person.

By RAF inhibitor, for example a BRAF inhibitor, is meant a compound that reduces the biological activity of RAF, for example BRAF; or that reduces the expression of an mRNA encoding a RAF polypeptide, for example BRAF; or that reduces the expression of a RAF polypeptide, for example BRAF. RAF kinase inhibitors are well known to the skilled person. Any suitable RAF inhibitor clinically or pharmaceutically indicated for the treatment of cancer, e.g. melanoma, may be used in the present invention. Non-limitative examples of RAF inhibitors include the compounds GW5074, BAY 43-9006, CHIR-265 (Novartis), Vemurafenib, PLX4720 (Tsai et al. 2008 PNAS 105(8):3041), PLX4032 (RG7204), GDC-0879 (Klaus P. Hoeflich et al. Cancer Res. 2009 Apr. 1; 69:3042-3051), sorafenib tosylate (e.g. from Bayer and Onyx Pharmaceuticals as Nexavar), dasatinib (also known as BMS-354825, e.g. as produced by Bristol-Myers Squibb and sold under the trade name Sprycel), erlotinib (e.g. as marketed by Genentech and OSI pharmaceuticals as Tarceva), LGX818 from Novartis, dabrafenib (Tafinlar™ capsule, made by GlaxoSmithKline, LLC), dabrafenib, gefitinib, imatinib mesilate, lapatinib, sunitinib malate, GSK2118436, and benzenesulfonamide.

A MEK polypeptide (e.g. Gene accession numbers 5604 or 5605; Refseq RNA Accessions NM_002755.3 or NM_030662.3; protein NP_002746.1 or NP_109587.1), protein or peptide is to indicate a polypeptide having serine/threonine protein kinase activity. For example MEK1 (e.g. Genbank Accession NO: NP002746) and MEK2 (e.g. Genbank Accession NO: NP109587) phosphorylates and activates MAPK. Another example is MEK3 ((e.g. Genbank Accession NO: NP002747). MEK comprises both MEK1 and MEK2: MAP/ERK kinase 1, MEK1, PRKMK1, MAPKK1, MAP2K1, MKK1 are the same enzyme, known as MEK1, MAP/ERK kinase 2, MEK2, PRKMK2, MAPKK2, MAP2K2, MKK2 are the same enzyme, known as MEK2. MEK1 and MEK2, together MEK, can phosphorylate serine, threonine and tyrosine residues in protein or peptide substrates. By MEK inhibitor is meant a compound that reduces the biological activity of MEK; or that reduces the expression of an mRNA encoding a MEK polypeptide; or that reduces the expression of a MEK polypeptide. A MEK inhibitor can inhibit one member, several members or all members of the family of MEK kinases. In one embodiment the MEK inhibitor is a selective inhibitor. Any suitable MEK inhibitor clinically or pharmaceutically indicated for the treatment of cancer, e.g. melanoma, may be used in the present invention. Examples of MEK inhibitors, include but are not limited to the MEK inhibitors PD184352 and PD98059, inhibitors of MEKI and MEK2 U0126 (see Favata, M., et al., J. Biol. Chem. 273, 18623, 1998) and SL327 (Carr et al Psychopharmacology (Berl). 2009 January; 201(4):495-506), and those MEK inhibitors discussed in Davies et al (2000) (Davies et al Biochem J. 351, 95-105). Another example is PDI 84352 (Allen, Lee et al Seminars in Oncology, October 2003, pp. 105-106, vol. 30) or GSK1120212/Trametinib, which has been approved for treatment of BRAF mutant melanoma under the name Mekinist. MEK162 (Array pharma) is also preferred. Other MEK inhibitors and classes of MEK inhibitors are described in Zhang et al. (2000) Bioorganic & Medicinal Chemistry Letters; 10:2825-2828. Furthermore, the MEK inhibitor may be selected from PD-325901 (Phase 1, Pfizer), XL518 (Phase 1, Genentech), PD-184352 (Allen and Meyer Semin Oncol. 2003 October; 30 (5 Suppl 16):105-16.), PD-318088 (Tecle et al nic & Medicinal Chemistry Letters Volume 19, Issue 1, 1 Jan. 2009, Pages 226-229), AZD6244 (selumetinib, Phase II, Dana Farber, AstraZeneca; WO2007/076245.), CI-1040 (Lorusso et al Journal of clinical oncology 2005, vol. 23, no 23, pp. 5281-5293), trametinib, TAK-733, Selumetinib, Trametinib, Cobimetinib or XL518 or Honokiol. Another preferred example is binimetinib.

In another embodiment the MEK inhibitor may inhibit (gene) expression of MEK, for example by interfering with mRNA stability or translation. In one embodiment the MEK inhibitor is selected from small interfering RNA (siRNA), which is sometimes known as short interfering RNA or silencing RNA, or short hairpin RNA (shRNA), which is sometimes known as small hairpin RNA. The skilled person knows how to design such small interfering nucleotide sequence, for example as described in handbooks such as Doran and Helliwell RNA interference: methods for plants and animals Volume 10 CABI 2009.

An ERK polypeptide or peptide is to indicate a polypeptide having serine/threonine protein kinase activity, e.g. ERK phosphorylates and activates MAP (microtubule-associated proteins), and having at least 85% amino acid identity to the amino acid sequence of a human ERK, e.g. to ERK1 (e.g. Gene accession number 5595; Refseq RNA Accessions NM_001040056.2; protein NP_001035145.1) or ERK2 (e.g. Gene accession number 5594; Refseq RNA Accessions NM_002745.4; protein NP_002736.3). By ERK inhibitor is meant a compound that reduces the biological activity of ERK; or that reduces the expression of an mRNA encoding an ERK polypeptide; or that reduces the expression of an ERK polypeptide. An ERK inhibitor can inhibit one member, several members or all members of the family of ERK kinases. ERK inhibitors are well-known to the skilled person. Any suitable ERK inhibitor clinically or pharmaceutically indicated for the treatment of cancer, e.g. melanoma, may be used in the present invention. Non-limiting examples of ERK inhibitors include compounds disclosed in WO2002058687, for example SL-327 (Carr et al Psychopharmacology (Berl). 2009 January; 201(4):495-5060). Further ERK inhibitors may be found in WO2002058687, AU2002248381, US20050159385, US2004102506, US2005090536, US2004048861, US20100004234, HR20110892, WO2011163330, TW200934775, EP2332922, WO2011041152, US2011038876, WO2009146034, HK1117159, WO2009026487, WO2008115890, US2009186379, WO2008055236, US2007232610, WO2007025090, and US2007049591. Further non-limiting examples or ERK-inhibitors include BVD-523, FR 180204 (CAS No. 865362-74-9), Hypothemycin (CAS no. 76958-67-3), MK-8353, SCH9003531, Pluripotin (CAS no. 839707-37-8), SCH772984 (CAS no. 942183-80-4), and VX-11e (Cas no. 896720-20-0).

RSK polypeptide (e.g. EC 2.7.11.1; e.g. Gene accession numbers 6195, 6197, 6196, or 27330; Refseq RNA Accessions NM_001006665, NM_002953, NM_004586, NM_001006932, NM_021135, or NM_014496; protein NP_001006666.1, NP_004577.1, NP_001006933.1, or NP_055311.1), protein or peptide is to indicate a protein of the ribosomal s6 kinase (rsk) a family of protein kinases. There are two subfamilies of rsk, p90RSK, also known as MAPK-activated protein kinase-1 (MAPKAP-K1), and p70RSK, also known as S6-H1 Kinase or simply S6 Kinase. The RSK protein is a MAP kinase activated protein kinase (MAPKAP kinase) and described in, e.g., Leukemia, 17: 1263-1293 (2003). RSK is phosphorylated and activated by ERK1 and -2 in response to many growth factors, polypeptide hormones and neurotransmitters. RSK inhibitors are well-known to the skilled person. Any suitable RSK inhibitor clinically or pharmaceutically indicated for the treatment of cancer, e.g. melanoma, may be used in the present invention. Non-limiting examples of RSK inhibitors include, for example, Kaempherol-3-O-(4'-O-acetyl-a-L-rhamnopyranoside), or such inhibitors as disclosed in EP1845778. Other inhibitor may inhibit (gene) expression of RSK, for example by interfering with mRNA stability or translation. In one embodiment the RSK inhibitor is selected from small interfering RNA (siRNA), which is sometimes known as short interfering RNA or silencing RNA, or short hairpin RNA (shRNA), which is sometimes known as small hairpin RNA. The skilled person knows how to design such small interfering nucleotide sequence, for example as described in handbooks such as Doran and Helliwell RNA interference: methods for plants and animals Volume 10 CABI 2009. The activity of RSK protein or inhibitory activity of a RSK inhibitor can be determined by the method described in, e.g., EMBO J., 14: 674-684 (1995) or in EP1845778./pct Preferred examples of RAF inhibitors include Vemurafenib (Roche/Plexxikon), Dabrafenib (GSK), LGX818 (Novartis), TAK-632 (Takeda), MLN2480 (Takeda/Millennium), PLX-4720 (Plexxikon).

Preferred examples of MEK inhibitors include Trametinib (GSK), Cobimetinib (GDC-0973) (Genentech/Exelixis), MEK162 (Novartis/Array BioPharma), AZD6244 (AstraZeneca/Array BioPharma), RO5126766 (Roche/Chugai), GDC-0623 (Genentech/Chugai), PD0325901 (Pfizer), Selumetinib, and binimetinib.

Preferred examples of ERK inhibitors include SCH772984 (Merck/Schering-Plough), VTX11e (Vertex), GDC-0994 (Roche/Genentech).

The BRAF- and/or NRAS-mutation harboring melanoma to be treated with the HDACi, in this aspect of the invention, may have acquired resistance to an inhibitor of the MAPK inhibitor.

The term acquired resistance within the context of response to a MAPK pathway inhibitor is well-known to the skilled person. It is a well-documented fact that chronic treatment of subjects with MAPK pathway inhibitors is very often associated with the development of drug resistance, i.e. the melanoma becomes less responsive to the MAPK pathway inhibitor and acquires resistance to a MAPK pathway inhibitor. This means that the melanoma does not, or to a lesser extent, respond anymore (i.e., as measured by the lack of induction of apoptosis or lack of growth arrest when a MAPK pathway inhibitor is applied to such a MAPK pathway inhibitor resistant melanoma) to the MAPK inhibitor treatment. In daily practice, resistance to, for example vemurafenib, resistance develops on average within 7 months of initial use, as is witnessed by a decrease in initial favorable response to the drug (i.e. less tumor regression, or return of tumor growth after initial stabilization, or as determined by measuring response or expression/activity of marker genes or proteins (e.g. of the MAPK pathway) of cell obtained from the subject by biopsies; see for example Trunzer et al. J Clin Oncol. 2013 May 10; 31(14):1767-74. doi: 10.1200/JCO.2012.44.7888).

Within the context of the current invention, the melanoma has acquired resistance to a MAPK pathway inhibitor. The resistance may the consequence of prior chronic exposure to said MAPK pathway inhibitor or to another MAPK pathway inhibitor, for example directed to the same protein (RAS, RAF, ERK, MEK, RSK) of the MAPK pathway, or to another protein of the MAPK pathway (for example, it may be envisaged that a melanoma may acquire resistance to a ERK inhibitor as the consequence of (chronic) exposure to a BRAF inhibitor and/or a MEK inhibitor.

As will be understood by the skilled person, resistance to a MAPK pathway inhibitor may also be acquired by exposure to a combination of MAPK pathway inhibitors.

It was surprisingly found that the treatment of the BRAF- and/or NRAS-mutation harboring melanoma that acquired resistance to a MAPK pathway inhibitor should be done under conditions that do not involve simultaneous treatment with a MAPK pathway inhibitor, for example the MAPK pathway inhibitor for which the melanoma cells acquired resistance.

In other words, in the disclosures, a HDACi is only provided to the patient after the treatment with a MAPK pathway inhibitor is discontinued. It was found that combined treatment with a MAPK pathway inhibitor and a HDACi shows antagonistic effects and limits the anti-cancer effect whereas the sequential treatment with first a MAPK pathway inhibitor and, once the melanoma acquires resistance to a MAPK pathway inhibitor, discontinuation of the treatment with the MAPK pathway inhibitor and, after the discontinuation, followed by the provision of the HDACi provides for improved treatment of the melanoma.

With treatment with a MAPK pathway inhibitor is meant the (repeated) provision of an amount of a MAPK pathway inhibitor to a patient that is believed to provide clinical benefit to the patient suffering from a melanoma that has not acquired resistance to a MAPK pathway inhibitor. Treatment generally involves the repeated provision of a dosage of the drug to the patient and for a longer period. Discontinuation of a treatment means stopping the treatment of the patient with a given drug.

With treatment with a HDACi is meant the provision of an amount of a HDACi to a patient that is believed to provide clinical benefit to the patient suffering from a melanoma after the melanoma has acquired resistance to a MAPK pathway inhibitor. Treatment generally involves the repeated provision of a dosage of the drug to the patient and for a longer period. In the treatment according to the invention, as long has the HDACi is used to treat the patient (i.e. repeatedly provided to the patient) the patient in not treated with a MAPK pathway inhibitor.

The skilled person knows how to treat with the HDACi (and/or xTCi) while not at the same time treating with a MAPK pathway inhibitor (i.e. in a manner so that the HDACi and the MAPK pathway inhibitor are not jointly therapeutically active in the patient or subject receiving the treatment). In contrast to combined treatment, the HDACi is provided to a subject such that it does not interact (no joint therapeutic action) with any MAPK pathway inhibitor present in the same subject within the context of the treatment of the patient.

The skilled person may for example, before providing the HDACi measure (e.g. in the blood or plasma, etc.) the presence of any MAPK pathway inhibitor previously provided to the subject in view of the treatment of melanoma and decide to provide the HDACi to the subject only once the concentration of the MAPK pathway inhibitor reaches a certain level (e.g. level that are too low or insufficient to allow joint therapeutic action or any pharmaceutical or chemical interaction between the HDACi and the MAPK pathway inhibitor) after discontinuation of the treatment with the MAPK pathway inhibitor.

Alternatively, and in practice, the HDACi is provided to the subject only after a certain time has passed since the treatment with the MAPK pathway inhibitor was discontinued.

Preferably also the treatment with the MAPK pathway inhibitor does not involve the simultaneous treatment with an HDACi. In other words, in the treatment of the melanoma with the MAPK pathway inhibitor, and before the melanoma acquires resistance to a MAPK pathway inhibitor, the treatment with MAPK pathway inhibitor (or combination of MAPK pathway inhibitors) is not combined with the treatment with a HDACi.

It is thus, within the context of the treatment of BRAF- and/or NRAS-mutation harboring melanoma preferred that the treatment with the MAPK-pathway inhibitor before the melanoma acquires resistance does not involve the combined treatment with a HDACi, and it is required that the treatment with the HDACi after the melanoma has acquired resistance to the MAPK pathway inhibitor is does not involve the combined treatment with a MAPK pathway inhibitor.

Experimentation by the inventors established that the invention is not limited to one specific HDACi. Although any HDACi, or combination of HDACi, may be used in the invention, in a preferred embodiment the HDACi is vorinostat, CXD-101, entinostat, 01994, AR42, practinostat, quisinostat, panobinostat, belinostat, romidepsin or combinations thereof.

Moment of administration, dosage, dosage forms and regimen for the HDACi for use in the treatment can be established by the skilled person using routine experimentation.

In a preferred embodiment the melanoma is a BRAF-mutation harboring melanoma. Indeed, for all aspects of the current invention. In another preferred embodiment the melanoma is a NRAS-mutation harboring melanoma. The skilled person is well-aware of techniques establishing whether a melanoma is a melanoma harboring NRAS- and/or BRAF-mutations. For example by using DNA sequencing techniques and the information disclosed herein.

In another preferred embodiment of the invention, the MAPK pathway inhibitor the melanoma has acquired resistance to is a RAS inhibitor, a RAF inhibitor, a MEK inhibitor, an ERK inhibitor and/or a RSK inhibitor. In other words, the melanoma that is to be treated with the HDACi is a melanoma that has acquired resistance to a RAS inhibitor, a RAF inhibitor, a MEK inhibitor, an ERK inhibitor and/or a RSK inhibitor.

In another preferred embodiment, the treatment with the HDACi does not involve the simultaneous treatment with a RAS inhibitor, a RAF inhibitor, a MEK inhibitor, an ERK inhibitor and/or a RSK inhibitor, so that there is no joint therapeutic actions between the HDACi and the RAS inhibitor, RAF inhibitor, MEK inhibitor, ERK inhibitor and/or RSK inhibitor.

Experiments performed by the current inventor show that the MAPK pathway inhibitor, for example the RAS inhibitor, RAF inhibitor, MEK inhibitor, ERK inhibitor and/or RSK inhibitor to which the melanoma acquires resistance, or put in other words, with which the melanoma is treated before it acquires resistance to a MAPK pathway inhibitor is not particularly limited.

Obviously when a subject is treated with such MAPK pathway inhibitor, for example the RAS inhibitor, RAF inhibitor, MEK inhibitor, ERK inhibitor and/or RSK inhibitor, the inhibitor is a clinically or pharmaceutically acceptable inhibitor, in other words, is suitable for use in treatment of melanoma in the subject, in particular a human.

In a preferred embodiment the RAS inhibitor, RAF inhibitor, MEK inhibitor, ERK inhibitor and/or a RSK inhibitor is vemurafenib, dabrafenib, trametinib, LGX-818, cobimetinib, selumetinib, PD-0325901, MEK162, or SCH772984, binimetinib or combinations thereof.

Preferred examples of RAF inhibitors include Vemurafenib (Roche/Plexxikon), Dabrafenib (GSK), LGX818 (Novartis), TAK-632 (Takeda), MLN2480 (Takeda/Millennium), PLX-4720 (Plexxikon).

Preferred examples of MEK inhibitors include Trametinib (GSK), Cobimetinib (GDC-0973) (Genentech/Exelixis), MEK162 (Novartis/Array BioPharma), AZD6244 (AstraZeneca/Array BioPharma), RO5126766 (Roche/Chugai), GDC-0623 (Genentech/Chugai), PD0325901 (Pfizer), Selumetinib and binimetinib.

Preferred examples of ERK inhibitors include SCH772984 (Merck/Schering-Plough), VTX11e (Vertex), GDC-0994 (Roche/Genentech).

In another preferred embodiment the treatment with the HDACi after the cells have acquired resistance to a MAPK pathway inhibitor does not involve the combined treatment with any MAPK pathway inhibitor. In this embodiment, and independent of to what MAPK pathway inhibitor and/or to what inhibitor of RAS, RAF, MEK, ERK and/or RSK the melanoma acquired resistance, the resistant melanoma is treated with the HDACi in the absence of any compound that, within the context of the current invention, is an inhibitor of the MAPK pathway, more in particular in the absence of any inhibitor of RAS, RAF, MEK, ERK and RSK. In other words, there is no joint therapeutic action of the HDACi and the MAPK pathway inhibitor.

The skilled person will understand that an inhibitor of the MAPK pathway and within the context of the current invention is a compound that at the used concentration is known to or shown to inhibit one or more proteins of the MAPK pathway, in particular one or more of RAS, RAF, MEK, ERK, and/or RSK, preferably when provided to a subject, preferably a human, to such extent it may be used in treatment of melanoma in order to provide clinical benefit.

As explained herein, the current invention is based on the realization that, in contrast to suggestions in the art, a MAPK pathway inhibitor and a HDACi should not be combined in the treatment of NRAS- and/or BRAF-mutated melanoma, in particular not in such melanoma that as acquired resistance to a MAPK pathway inhibitor and that treatment of such melanoma is improved when the melanoma that acquired resistance to a MAPK pathway inhibitor is treated with a HDACi under conditions that the treatment with the HDACi is not combined with a MAPK pathway inhibitor. In other words, before the HDACi is used to treat the melanoma that acquired resistance to a MAPK pathway inhibitor, treatment with a MAPK pathway inhibitor is discontinued, allowing the body of the subject treated with the MAPK pathway inhibitor to remove the MAPK pathway inhibitor from the system (so that MAPK pathway inhibitor levels in the cells are too low or undetectable or insufficient to allow joint therapeutic action with HDACi). The HDACi is administered to the subject once the concentration or amount of the MAPK pathway inhibitor reaches a certain level at which the antagonistic effects of the combined use of the MAPK pathway inhibitor and the HDACi have become clinically irrelevant or absent. It will be understood that the exact conditions under which the HDACi may be administered to the subject after discontinuation of the MAPK pathway inhibitor will depend of factors such as the type and dosage of MAPK pathway inhibitor used and the type and dosage of the HDACi used, as that such conditions may be established by the skilled person using routine experimentation.

In a preferred embodiment, the HDACi treatment starts within a period of 1-28 days after treatment with the MAPK pathway is discontinued. For example, the treatment with the HDACi starts 1, 2, 3, 4, 5 ... 10 ... 15 ... 20 ... 28 days after the treatment with the MAPK pathway inhibitor is discontinued. Such periods between the last dosage of the MAPK pathway inhibitor and the first dosage of the HDACi will in most cases be sufficient. Depending on, for example the MAPK pathway inhibitor used and/or the condition of the patient, the first administration of the HDACi may be even shorter after the last administration of the MAPK pathway inhibitor, as long as the MAPK pathway inhibitor and the HDACi do not interact/the treatment with the MAPK pathway inhibitor is, from a clinical point, considered to be discontinued.

In another embodiment of the invention, when the MAPK pathway inhibitor the melanoma has acquired resistance to is a RAS inhibitor, a RAF inhibitor, a MEK inhibitor, an ERK inhibitor and/or a RSK inhibitor, the treatment with the HDACi does not involve the simultaneous treatment with a RAS inhibitor, a RAF inhibitor, a MEK inhibitor, an ERK inhibitor and/or a RSK inhibitor respectively. In such embodiment, when the melanoma has acquired resistance to an inhibitor of, for example, MEK, it is advantageous that, in this example, in particular the MEK inhibitor is avoided during the treatment with the HDACi. In principal, in this embodiment, an inhibitor to another then, in the example, MEK, may be present, however, as explained above, it is a preferred embodiment that any inhibitor of the MAPK pathway is avoided after the melanoma acquired resistance to a MAPK pathway inhibitor, independent whether the melanoma acquired resistance to a RAS, RAF, ERK, MEK or RSK inhibitor.

The invention also provides for a HDACi for use in in the treatment of a subject with melanoma characterized in that the melanoma is a BRAF-mutation or a NRAS-mutation harboring melanoma wherein the treatment comprises treatment with a MAPK pathway inhibitor followed by treatment with a HDACi after the melanoma has acquired resistance to a MAPK pathway inhibitor and wherein said treatment with the HDACi does not involve the simultaneous treatment with a MAPK pathway inhibitor.

In other words, in this embodiment of the invention the HDACi is used in the treatment of melanoma that has been treated with a MAPK pathway inhibitor. In this embodiment the melanoma is first treated with a MAPK pathway inhibitor. After the melanoma acquires resistance to a MAPK pathway inhibitor, the treatment with the MAPK pathway inhibitor is stopped/discontinued, after which the melanoma is treated with the HDACi in the absence of treatment with a MAPK pathway inhibitor, so that there is no joint therapeutic action between the HDACi and the MAPK pathway inhibitor.

It will be understood by the skilled person than any preference or exclusion discussed herein with respect other embodiments/aspects of the invention are likewise applicable to this embodiment/aspect of the invention. For example, in a preferred embodiment, the treatment with the MAPK pathway inhibitor (before the melanoma becomes resistant) preferably also does not involve the combined treatment with a HDACi.

Also provided is for use of a HDACi in the manufacture of a medicament for the treatment of a subject with melanoma characterized in that the melanoma is a BRAF-mutation or a NRAS-mutation harboring melanoma that has acquired resistance to a MAPK pathway inhibitor and wherein the treatment with the HDACi does not involve the simultaneous treatment with a MAPK pathway inhibitor.

It will be understood by the skilled person than any preference or exclusion discussed herein with respect other embodiments/aspects of the invention are likewise applicable to this embodiment/aspect of the invention.

Also provided is use of a HDACi in the manufacture of a medicament for the treatment of a subject with melanoma characterized in that the melanoma is a BRAF-mutation or a NRAS-mutation harboring melanoma wherein the treatment comprises treatment with a MAPK pathway inhibitor followed by treatment with a HDACi after the melanoma has acquired resistance to a MAPK pathway inhibitor and wherein said treatment with the HDACi does not involve the simultaneous treatment with a MAPK pathway inhibitor.

It will be understood by the skilled person than any preference or exclusion discussed herein with respect other embodiments/aspects of the invention are likewise applicable to this embodiment/aspect of the invention. For example, in a preferred embodiment, the treatment with the MAPK pathway inhibitor (before the melanoma becomes resistant) preferably also does not involve the combined treatment with a HDACi. After the melanoma acquires resistance to the MAPK pathway inhibitor, for example a MEK, BRAF or ERK inhibitor, or combinations thereof, the treatment with the MAPK pathway inhibitor(s) is discontinued.

Also provided is a MAPK pathway inhibitor for use in the treatment of a subject with melanoma characterized in that the melanoma is a BRAF-mutation or a NRAS-mutation harboring melanoma wherein the treatment comprises treatment with the MAPK pathway inhibitor followed by treatment with a HDACi after the melanoma has acquired resistance to a MAPK pathway inhibitor and wherein said treatment with the HDACi does not involve the simultaneous treatment with a MAPK pathway inhibitor.

It will be understood by the skilled person than any preference or exclusion discussed herein with respect other embodiments/aspects of the invention are likewise applicable to this embodiment/aspect of the invention. For example, in a preferred embodiment, the treatment with the MAPK pathway inhibitor (before the melanoma becomes resistant) preferably also does not involve the combined treatment with an HDACi. After the melanoma acquires resistance to the MAPK pathway inhibitor(s), the treatment with the MAPK pathway inhibitor(s) is discontinued.

Also provided for use of a MAPK pathway inhibitor in in the manufacture of a medicament for the treatment of a subject with melanoma characterized in that the melanoma is a BRAF-mutation or a NRAS-mutation harboring melanoma wherein the treatment comprises treatment with the MAPK pathway inhibitor followed by treatment with a HDACi after the melanoma has acquired resistance to a MAPK pathway inhibitor and wherein said treatment with the HDACi does not involve the simultaneous treatment with a MAPK pathway.

It will be understood by the skilled person than any preference or exclusion discussed herein with respect other embodiments/aspects of the invention are likewise applicable to this embodiment/aspect of the invention.

In an aspect of the invention there is provided for a method of treatment of a subject, preferably a human.

The method is a method of treating a subject with melanoma characterized in that the melanoma is a BRAF-mutation or a NRAS-mutation harboring melanoma, the method comprising:
  a) Treating said subject with a therapeutically acceptable amount of a MAPK pathway inhibitor;
  b) Discontinuing treating the subject with said therapeutically acceptable amount of a MAPK pathway inhibitor when the melanoma has acquired resistance to a MAPK pathway inhibitor;
  c) Treating said subject with a therapeutically acceptable amount of a HDACi.

Again, it will be understood by the skilled person than any preference or exclusion discussed herein with respect other embodiments/aspects of the invention are likewise applicable to this embodiment/aspect of the invention.

In a preferred embodiment, step c) starts within a period of 1-28 days after step b), as already explained in detail herein.

In a preferred embodiment, step a) the treatment does not involve the simultaneous treatment with an HDACi, as already explained in detail herein.

There is also provided for method of treating a subject with melanoma characterized in that the melanoma is a BRAF-mutation or a NRAS-mutation harboring melanoma that has acquired resistance to a MAPK pathway inhibitor the method comprising
  a) Treating said subject with a therapeutically acceptable amount of a HDACi, wherein the treatment with the HDACi does not involve the simultaneous treatment with a MAPK pathway inhibitor (in other words there is no joint therapeutic action between the HDACi and the MAPK pathway inhibitor).

Again, it will be understood by the skilled person than any preference or exclusion discussed herein with respect other embodiments/aspects of the invention are likewise applicable to this embodiment/aspect of the invention.

A further aspect pertaining to the present invention relates to the mechanism by which the HDACi as taught herein exert their beneficial effect in the treatment of subjects with melanoma characterized in that the melanoma is a BRAF-mutation or a NRAS-mutation harboring melanoma that has acquired resistance to a mitogen-activated protein kinase (MAPK) pathway inhibitor.

The present inventors have found that treatment with a HDAC inhibitor is associated with or causes the down-regulation of a protein referred to as XCT (also known as SCL7A11), as shown in the examples therein. The term "XCT" or "SCL7A11" as used herein, refers to a cystine-glutamate antiporter that serves a transmembrane transporter capable of importing cystine into the cell, which serves as a precursor to reduced glutathione (GSH). GSH is one of the major endogenous antioxidant co-factors within the cells. Under normal situation, GSH is required to inactivate reactive oxygen species (ROS) in cells. High levels of ROS are detrimental (e.g. cause cell death or decreased cell survival) to cell function under normal condition It was further found that abolishing the endogenous expression of XCT in a cell (e.g. knocking down the expression) caused: 1) an increased in ROS levels in said cells, and 2) increased cell death or decreased cell survival. Similarly, it was found that inhibiting the function or expression of XCT (e.g. DNA, mRNA and/or protein) in a cell (e.g. melanoma) using a XCT inhibitor (e.g. sulfasalazine) produced similar effects, i.e. increased cell death or decreased cell survival of cancer cells (e.g. melanoma cells) treated with said compound.

It was further surprisingly found that treatment with HDACi in combination with a XCTi worked better due to a synergetic effect (i.e. more cell death or cell survival was decreased to a greater extent) that treatment with the individual compounds, as shown herein in the experimental section.

A further surprising effect is that the effects mentioned above were more pronounced in melanoma cells (i.e. a BRAF-mutation or a NRAS-mutation harboring melanoma) that are resistant or have acquired resistance to MAPK pathway inhibitors, as shown herein in the experimental section.

Without being bound to any theories, it is believed that the down-regulation of XCT may mediate or underlie or may explain, at least in part, the anti-cancer effect of HDACi, treatment as disclosed herein, causing cell death or decreased survival of BRAF-mutation or a NRAS-mutation harboring melanoma cells.

In other words, it is believed that a reduced abundance or down-regulation of XCT protein or XCT DNA and/or XCT mRNA levels and/or XTC protein levels or activity in a cell, e.g. BRAF-mutation or a NRAS-mutation harboring melanoma cell, causes a decrease or down-regulation or depletion of GSH levels in said cells which in turn leads to an increase in ROS levels in cells, i.e. inactivation of ROS is impaired or reduced in said cells.

Therefore, in a further aspect, the present invention relates to embodiments where the treatment of a subject with melanoma characterized in that the melanoma is a BRAF-mutation or a NRAS-mutation harboring melanoma that has acquired resistance to MAPK pathway inhibitor may be performed with a XCTi, as taught above, since it leads to or causes similar anti-cancer effects, causing increased cell death or decreased cell survival, as treatment with HDACi alone.

In another further aspect, the present invention relates to embodiments where the treatment of a subject with melanoma characterized in that the melanoma is a BRAF-mutation or a NRAS-mutation harboring melanoma that has acquired resistance to MAPK pathway inhibitor may be performed with a HDACi and a XCTi, as taught above, since it leads to or causes enhanced anti-cancer effects, causing increased cell death or decreased cell survival as treatment with HDACi alone.

It is understood that, with respect to embodiments relating to the use of a XCTi or the use of HDACi in combination with a XCTi for the treatment of a subject with melanoma characterized in that the melanoma is a BRAF-mutation or a NRAS-mutation harboring melanoma that has acquired resistance to a MAPK pathway inhibitor, the content or preference or exclusion discussed herein with respect other embodiments or aspects of the invention relating to the use of HDACi for the same purpose are likewise applicable to the embodiments below unless specified otherwise. Particularly, it is understood that treatment with a XCTi or treatment with a HDACi in combination with a XCTi is performed in a manner so that there is no joint therapeutic action between the XCTi and the MAPK pathway inhibitor or no joint therapeutic action between the HDACi in combination with the XCTi and the MAPK pathway inhibitor, as taught above. Therefore, it is clear that there is no need to repeat these elements of the text and as well as other related elements (e.g. type of MAPK pathway inhibitors, melanoma cancer mutation type, etc) in the embodiments below.

Treatment with a XCTi

In a further aspect, the present invention relates to a XCT inhibitor (XCTi) for use in the treatment of a subject with melanoma characterized in that the melanoma is a BRAF-mutation or a NRAS-mutation harboring melanoma that has acquired resistance to a mitogen-activated protein kinase (MAPK) pathway inhibitor and wherein the treatment with the XCTi does not involve the simultaneous treatment with a MAPK pathway inhibitor. In an embodiment, the subject may have been previously treated with a MAPK pathway inhibitor.

In an embodiment, the XCTi may be any suitable compound capable of inhibiting or down-regulating or reducing the expression or levels (e.g. DNA, mRNA, protein levels) of XCT in a cell, for instance a cancer cell (e.g. BRAF-mutation or a NRAS-mutation harboring melanoma).

In an embodiment, the XCTi may be selected from the group consisting of sulfasalazine and erastin, preferably sulfasalazine.

In an embodiment, the melanoma may be a BRAF-mutation harboring melanoma.

In an embodiment, the melanoma may be a NRAS-mutation harboring melanoma.

In an embodiment, the MAPK pathway inhibitor the melanoma has acquired resistance to may be a RAS inhibitor, a RAF inhibitor, a MEK inhibitor, an ERK inhibitor and/or a RSK inhibitor.

In an embodiment, the treatment with the XCTi does not involve the simultaneous treatment with a MAPK pathway inhibitor, wherein the MAPK pathway inhibitor may be a RAS inhibitor, a RAF inhibitor, a MEK inhibitor, an ERK inhibitor and/or a RSK inhibitor.

In an embodiment, the RAS inhibitor, RAF inhibitor, MEK inhibitor, ERK inhibitor and/or RSK inhibitor may be vemurafenib, dabrafenib, trametinib, LGX-818, cobimetinib, selumetinib, PD-0325901, MEK162, SCH772984, binimetinib or combinations thereof.

In an embodiment, the treatment with the XCTi does not involve the simultaneous treatment with any MAPK pathway inhibitor.

In an embodiment, the XCTi treatment may start within a period of 1-28 days after treatment with the MAPK pathway is discontinued.

In an embodiment, when the MAPK pathway inhibitor the melanoma has acquired resistance to is a RAS inhibitor, a RAF inhibitor, a MEK inhibitor, an ERK inhibitor and/or a RSK inhibitor, the treatment with the XCTi does not involve the simultaneous treatment with a RAS inhibitor, a RAF inhibitor, a MEK inhibitor, an ERK inhibitor and/or a RSK inhibitor respectively.

In an embodiment relating to the treatment of a subject with melanoma characterized in that the melanoma is a BRAF-mutation or a NRAS-mutation harboring melanoma, the treatment may comprise treatment with a MAPK pathway inhibitor followed by treatment with a XCTi after the melanoma has acquired resistance to a MAPK pathway inhibitor and wherein said treatment with the XCTi does not involve the simultaneous treatment with a MAPK pathway inhibitor.

In an embodiment, the treatment with is the XTCi may be in combination with the treatment with a HDACi as taught herein.

In an embodiment, the present invention relates to the use of a XTCi in the manufacture of a medicament for the treatment of a subject with melanoma characterized in that the melanoma is a BRAF-mutation or a NRAS-mutation harboring melanoma that has acquired resistance to a MAPK pathway inhibitor and wherein the treatment with the XTCi does not involve the simultaneous treatment with a MAPK pathway inhibitor.

In embodiment relating to the use of a XTCi in the manufacture of a medicament, the treatment may comprise treatment with a MAPK pathway inhibitor followed by treatment with a XTCi after the melanoma has acquired resistance to a MAPK pathway inhibitor and wherein said treatment with the XTCi does not involve the simultaneous treatment with a MAPK pathway inhibitor.

In an embodiment, the present invention relates a MAPK pathway inhibitor for use in the treatment of a subject with melanoma characterized in that the melanoma is a BRAF-mutation or a NRAS-mutation harboring melanoma wherein the treatment may comprise treatment with the MAPK pathway inhibitor followed by treatment with a XTCi after the melanoma has acquired resistance to a MAPK pathway inhibitor and wherein said treatment with the XTCi does not involve the simultaneous treatment with a MAPK pathway inhibitor.

In an embodiment, the present invention relates to the use of a MAPK pathway inhibitor in the manufacture of a medicament for the treatment of a subject with melanoma characterized in that the melanoma is a BRAF-mutation or a NRAS-mutation harboring melanoma, wherein the treatment may comprise treatment with the MAPK pathway inhibitor followed by treatment with a XTCi after the melanoma has acquired resistance to a MAPK pathway inhibitor and wherein said treatment with the XTCi does not involve the simultaneous treatment with a MAPK pathway.

In an embodiment, the present invention relates to a method of treating a subject with melanoma characterized in that the melanoma is a BRAF-mutation or a NRAS-mutation harboring melanoma, the method comprising:

a) Treating said subject with a therapeutically acceptable amount of a MAPK pathway inhibitor;

b) Discontinuing treating the subject with said therapeutically acceptable amount of a MAPK pathway inhibitor when the melanoma has acquired resistance to a MAPK pathway inhibitor;

c) Treating said subject with a therapeutically acceptable amount of a XTCi.

In an embodiment, step c) may start within a period of 1-28 days after step b). In an embodiment, relating to step a), the treatment does not involve the simultaneous treatment with a XTCi.

In an embodiment, the present invention relates to a method of treating a subject with melanoma characterized in that the melanoma is a BRAF-mutation or a NRAS-mutation harboring melanoma that has acquired resistance to a MAPK pathway inhibitor the method comprising:

a) Treating said subject with a therapeutically acceptable amount of a XTCi, wherein the treatment with the XTCi does not involve the simultaneous treatment with a MAPK pathway inhibitor.

Treatment with a HDACi and/or a XCTi

Among the embodiments described below, the embodiments relating to treatment with an HDACi and a XCTi represent preferred embodiments of the present invention. In the present invention, treatment with a HDACi and a XCTi may be performed in a co-administration manner or in a combined administration manner as defined above, wherein the HDACi and the XCTi are jointly therapeutically active and wherein the HDACi and the XCTi are not jointly therapeutically active with a MAPK pathway inhibitor.

So, the present invention relates to a histone deacetylase inhibitor (HDACi) and/or XCT inhibitor (XCTi) for use in the treatment of a subject with melanoma characterized in that the melanoma is a BRAF-mutation or a NRAS-mutation harboring melanoma that has acquired resistance to a mitogen-activated protein kinase (MAPK) pathway inhibitor and wherein the treatment with the HDACi and/or XCTi does not involve the simultaneous treatment with a MAPK pathway inhibitor.

In an embodiment, the subject may have been previously treated with a MAPK pathway inhibitor.

In an embodiment, the HDACi may be selected as taught herein, for instance the HDACi may be selected from vorinostat, CXD-101, entinostat, 01994, AR42, practinostat, quisinostat, panobinostat, belinostat romidepsin or combinations thereof.

In an embodiment, the XCTi may be selected as taught herein, for instance the XCTi may be selected from the group consisting of sulfasalazine and erastin.

In an embodiment, the melanoma may be a BRAF-mutation harboring melanoma.

In an embodiment, the melanoma may be a NRAS-mutation harboring melanoma.

In an embodiment, the MAPK pathway inhibitor the melanoma has acquired resistance to may be a RAS inhibitor, a RAF inhibitor, a MEK inhibitor, an ERK inhibitor and/or a RSK inhibitor.

In an embodiment, the treatment with the HDACi and/or the XCTi does not involve the simultaneous treatment with a MAPK pathway inhibitor, wherein the MAPK pathway inhibitor may be a RAS inhibitor, a RAF inhibitor, a MEK inhibitor, an ERK inhibitor and/or a RSK inhibitor.

In an embodiment, the RAS inhibitor, RAF inhibitor, MEK inhibitor, ERK inhibitor and/or RSK inhibitor may be vemurafenib, dabrafenib, trametinib, LGX-818, cobimetinib, selumetinib, PD-0325901, MEK162, SCH772984, binimetinib or combinations thereof.

In an embodiment, the treatment with the HDACi and/or the XCTi does not involve the simultaneous treatment with any MAPK pathway inhibitor.

In an embodiment, the HDACi and/or XCTi treatment may start within a period of 1-28 days after treatment with the MAPK pathway is discontinued.

In an embodiment, when the MAPK pathway inhibitor the melanoma has acquired resistance to is a RAS inhibitor, a RAF inhibitor, a MEK inhibitor, an ERK inhibitor and/or a RSK inhibitor, the treatment with the HDACi and/or the XCTi does not involve the simultaneous treatment with a RAS inhibitor, a RAF inhibitor, a MEK inhibitor, an ERK inhibitor and/or a RSK inhibitor respectively.

In an embodiment relating to the treatment of a subject with melanoma characterized in that the melanoma is a BRAF-mutation or a NRAS-mutation harboring melanoma, the treatment may comprise treatment with a MAPK pathway inhibitor followed by treatment with a HDACi and/or a XCTi after the melanoma has acquired resistance to a MAPK pathway inhibitor and wherein said treatment with the HDACi and/or the XCTi does not involve the simultaneous treatment with a MAPK pathway inhibitor.

In an embodiment, the present invention relates to the use of a HDACi and/or a XTCi in the manufacture of a medicament for the treatment of a subject with melanoma characterized in that the melanoma is a BRAF-mutation or a NRAS-mutation harboring melanoma that has acquired resistance to a MAPK pathway inhibitor and wherein the treatment with the HDACi and/or the XTCi does not involve the simultaneous treatment with a MAPK pathway inhibitor.

In embodiment relating to the use of a HDACi and/or a XTCi in the manufacture of a medicament, the treatment may comprise treatment with a MAPK pathway inhibitor followed by treatment with a HDACi and/or a XTCi after the melanoma has acquired resistance to a MAPK pathway inhibitor and wherein said treatment with the HDACi and/or the XTCi does not involve the simultaneous treatment with a MAPK pathway inhibitor.

In an embodiment, the present invention relates to a MAPK pathway inhibitor for use in the treatment of a subject with melanoma characterized in that the melanoma is a BRAF-mutation or a NRAS-mutation harboring melanoma wherein the treatment may comprise treatment with the MAPK pathway inhibitor followed by treatment with a HDACi and/or a XTCi after the melanoma has acquired resistance to a MAPK pathway inhibitor and wherein said treatment with the HDACi and/or the XTCi does not involve the simultaneous treatment with a MAPK pathway inhibitor.

In an embodiment, the present invention relates to the use of a MAPK pathway inhibitor in the manufacture of a medicament for the treatment of a subject with melanoma characterized in that the melanoma is a BRAF-mutation or a NRAS-mutation harboring melanoma, wherein the treatment may comprise treatment with the MAPK pathway inhibitor followed by treatment with a HDACi and/or a XTCi after the melanoma has acquired resistance to a MAPK pathway inhibitor and wherein said treatment with the HDACi and/or the XTCi does not involve the simultaneous treatment with a MAPK pathway inhibitor.

In an embodiment, the present invention relates to a method of treating a subject with melanoma characterized in that the melanoma is a BRAF-mutation or a NRAS-mutation harboring melanoma, the method comprising:

a) Treating said subject with a therapeutically acceptable amount of a MAPK pathway inhibitor;

b) Discontinuing treating the subject with said therapeutically acceptable amount of a MAPK pathway inhibitor when the melanoma has acquired resistance to a MAPK pathway inhibitor;

c) Treating said subject with a therapeutically acceptable amount of a HDACi and/or a XTCi.

In an embodiment, step c) may start within a period of 1-28 days after step b). In an embodiment, relating to step a), the treatment does not involve the simultaneous treatment with a HDACi and/or a XTCi.

In an embodiment, the present invention relates to a method of treating a subject with melanoma characterized in that the melanoma is a BRAF-mutation or a NRAS-mutation harboring melanoma that has acquired resistance to a MAPK pathway inhibitor the method comprising:
a) Treating said subject with a therapeutically acceptable amount of a HDACi and/or a XTCi, wherein the treatment with the HDACi and/or the XTCi does not involve the simultaneous treatment with a MAPK pathway inhibitor.

Having now generally described the invention, the same will be more readily understood through reference to the following examples, which is provided by way of illustration and is not intended to be limiting of the present invention.

EXAMPLES

Example 1

Materials and Methods
Cell Lines

The A375 melanoma cell line was obtained from ATCC. MEL888 were gifts from D. Peeper (Amsterdam, The Netherlands). WM266-4 and Colo741 cell line were provided by R. Marais (Manchester, UK). These cells are BRAF mutated melanoma. All the cell lines were cultured in DMEM medium supplemented with 10% FBS, 1% penicillin/streptomycin and 2 mM I-glutamine. Vemurafenib-resistant A375 and MEL888 cells were generated by long term (at least 3 months) culturing with 2 microM vemurafenib. Dabrafenib-Trametinib combination resistant A375 cells were generated by long term (at least 3 months) culturing with 0.25 microM Dabrafenib and 10 nM Trametinib (MEK inhibitor). Vemurafenib-resistant ex-vivo clones were isolated from immunodeficient BalbC mice, which were long-term treated with PLX4720-chow (50 mg/kg). All the in vitro cell lines have been STR profiled.
Compounds, Antibodies and Reagents Vemurafenib (# S1267), vorinostat (# S1047), dabrafenib (# S2807), trametinib (# S2673), entinostat (# S1053), panobinostat (# S1030), elinostat (# S1085), and romideosin (# S3020) were purchased from Selleck Chemicals. PLX4720-Chow was produced by Research Diets Inc. PLX4720 was provided by Plexxikon. TGF-β1 was purchased from R&D (#240-B-010). Vorinostat (V-8477) used in in vivo experiment was purchased from LC Laboratories Antibodies against HSP90 (H-114), p21 (C-19), p-c-JUN (KM-1) and c-JUN (N), SHP2 (C-18), β-actin (C-2) were from Santa Cruz Biotechnology; anti-EGFR for western blot analysis (610017), RB (554136) and p27 (610242) antibodies were from BD Biosciences; Antibodies against cleaved-PARP (#5625), Histone 3 (#9715), p-RB (#9307), p-MEK (#9154), MEK (#4694) and PDGFRB (#4564, #3166) were from Cell Signaling; antibody against p-SHP2 (ab62322) was from Abcam; Antibody against VINC (062M4762) was from Sigma-Aldrich. Antibody against acetyl-Histone 3 (06-599) was from Millipore; antibody against α-tubulin (CP06) was from Calbiochem; antibody against RAS (1862335) was from Thermo Scientific.
Staining of β-Galactosidase Activity β-galactosidase activity in cells was detected using Histochemical Staining Kit (CS0030-1KT) from Sigma-Aldrich. The detection was applied according to the manufacturer's instructions.
Long-Term Cell Proliferation Assays Cells were seeded into 6-well plates ($5*10^4$~$1*10^5$ cells per well) or 12-well plates ($4*10^4$ cells per well) and cultured both in the absence and presence of drugs as indicated. For full details, see Huang et al. (2009) Cancer Cell 15, 328-340.
Protein Lysate Preparation and Immunoblots Cells were seeded in medium containing 10% fetal bovine serum (FBS) for indicated time, and then washed with PBS and lysed with RIPA buffer supplemented with protease inhibitor (cOmplete, Roche) and Phosphatase Inhibitor Cocktails II and III (Sigma). All lysates were freshly prepared and processed with Novex NuPAGE Gel Electrophoresis Systems (Invitrogen).

Active RAS Pull-Down Detection

RAS-GTP was detected using RAS Assay Reagent (RAF-1 RBD, agarose) from Merck Millipore. The detection was applied according to the manufacturer's instructions.

Mouse Xenografts

A375 melanoma cells ($2 \times 10^6$ cells per mouse) were injected subcutaneously into the right posterior flanks of 7-week-old immunodeficient BalbC or NMRI nude female mice (6 mice per group; Janvier Laboratories, The Netherlands). Tumor formation was monitored twice a week, and tumor volume based on caliper measurements was calculated by the modified ellipsoidal formula (tumor volume=½(length×width2)). When tumors reached a volume of approximately 0.3 cm³, mice were randomized into treatment arms. PLX4720 (Plexxikon) was formulated in the chow by Research Diets dosed at 300 mg/kg and vorinostat was formulated in DMSO/saline solution, and it was dosed at 100 mg per kg daily by intraperitoneal injection. When resistance to PLX4720 arises in the group treated with PLX4720, mice bearing tumors of approximately 0.3 cm³ were again randomized into the treatment arms with the same drug dosages. Animal experiments were approved by the Animal Ethics Committee of the Netherlands Cancer Institute and performed in accordance with institutional, national and European guidelines for Animal Care and Use.

Cell Line Samples

RNA isolation from cell lines harvested with TRIzol reagent (Invitrogen) according to the manufacturer's instruction. cDNA synthesis was performed with Maxima Universal First Strand cDNA Synthesis Kit (# K1661, Thermo scientific) according to manufacturer's instruction. The primers were used for qRT-PCR are described in Table 1 below.

TABLE 1

| Supplementary Table X qRT-PCR primers | SEQ ID NO. |
|---|---|
| EGFR | |
| TCCTCTGGAGGCTGAGAAAA | 1 |
| GGGCTCTGGAGGAAAAGAAA | 2 |
| GAPDH | |
| AAGGTGAAGGTCGGAGTCAA | 3 |
| AATGAAGGGGTCATTGATGG | 4 |
| SOX10 | |
| CTTTCTTGTGCTGCATACGG | 5 |
| AGCTCAGCAAGACGCTGG | 6 |
| PDGFRB | |
| CAGGAGAGACAGCAACAGCA | 7 |
| TGTCCAGAGCCTGGAACTGT | 8 |
| OCT | |
| CGACTCTGATTAGTCGGAACTCA | 9 |
| GGTGGTTGTAGTCATCCAAGC | 10 |
| TGFBR2 | |
| TCTGGTTGTCACAGGTGGAA | 11 |
| GCACGTTCAGAAGTCGGTTA | 12 |
| TAGLN | |
| GTCCGAACCCAGACACAAGT | 13 |
| CTCATGCCATAGGAAGGACC | 14 |

TABLE 1-continued

| Supplementary Table X qRT-PCR primers | SEQ ID NO. |
|---|---|
| CYR61 | |
| GCTGGAATGCAACTTCGG | 15 |
| CCCGTTTTGGTAGATTCTGG | 16 |
| CTGF | |
| TACCAATGACAACGCCTCCT | 17 |
| TGGAGATTTTGGGAGTACGG | 18 |
| ANGPTL4 | |
| GGAACAGCTCCTGGCAATC | 19 |
| GCACCTAGACCATGAGGTGG | 20 |
| BRAF | |
| GTGGATTATGCTCCCCACC | 21 |
| CTGCCATTCCGGAGGAG | 22 |

Results

BRAF Inhibition is Antagonized by HDAC Inhibition in Melanoma.

We studied the effects of drug combination treatment of BRAF mutant melanoma, in view of recent publications suggesting that a combination of BRAF inhibitor and HDAC inhibitor (HDACi) results in more potent anti-cancer effects than either drug alone (Johannessen et al. (2013) Nature 504, 138-142; Lai et al., (2013) Cell Death Dis 4, e655.). Treatment of BRAF mutant A375 melanoma cells with either the selective BRAF inhibitor vemurafenib or the HDACi vorinostat resulted in inhibition of proliferation (FIG. 1A, B). Unexpectedly, increasing concentrations of vorinostat almost completely negated the anti-proliferative effects of vemurafenib in long-term colony formation assays, suggesting an antagonism between these drugs (FIG. 1A). Consistently, in short-term cell proliferation assays, cells grown with drug-free culture medium proliferated almost as fast as cells treated with the combination of vemurafenib and vorinostat, whereas the same concentration of each drug alone restricted cell proliferation (FIG. 1B).

Treatment of A375 cells with vorinostat resulted in the induction of acidic beta-galactosidase, a marker associated with cell senescence (Michaloglou et al. (2005) Nature 436, 720-724.). Treatment of two different melanoma cell lines with vorinostat resulted in the loss of phosphorylation of pRB, induction of CDKN1A (p21cip1) and CDKN1B (p27kip1), effects that are also seen in senescent cells. Moreover, we observed that vorinostat treatment activated MEK kinases as judged by an increase in phospho-MEK (p-MEK) in both A375 and WM2664 melanoma cells. We interpret these results to indicate that HDACi treatment leads to a further activation of the MAP kinase pathway, which induces a state that has hallmarks of oncogene-induced senescence (OIS).

Figure 2A:
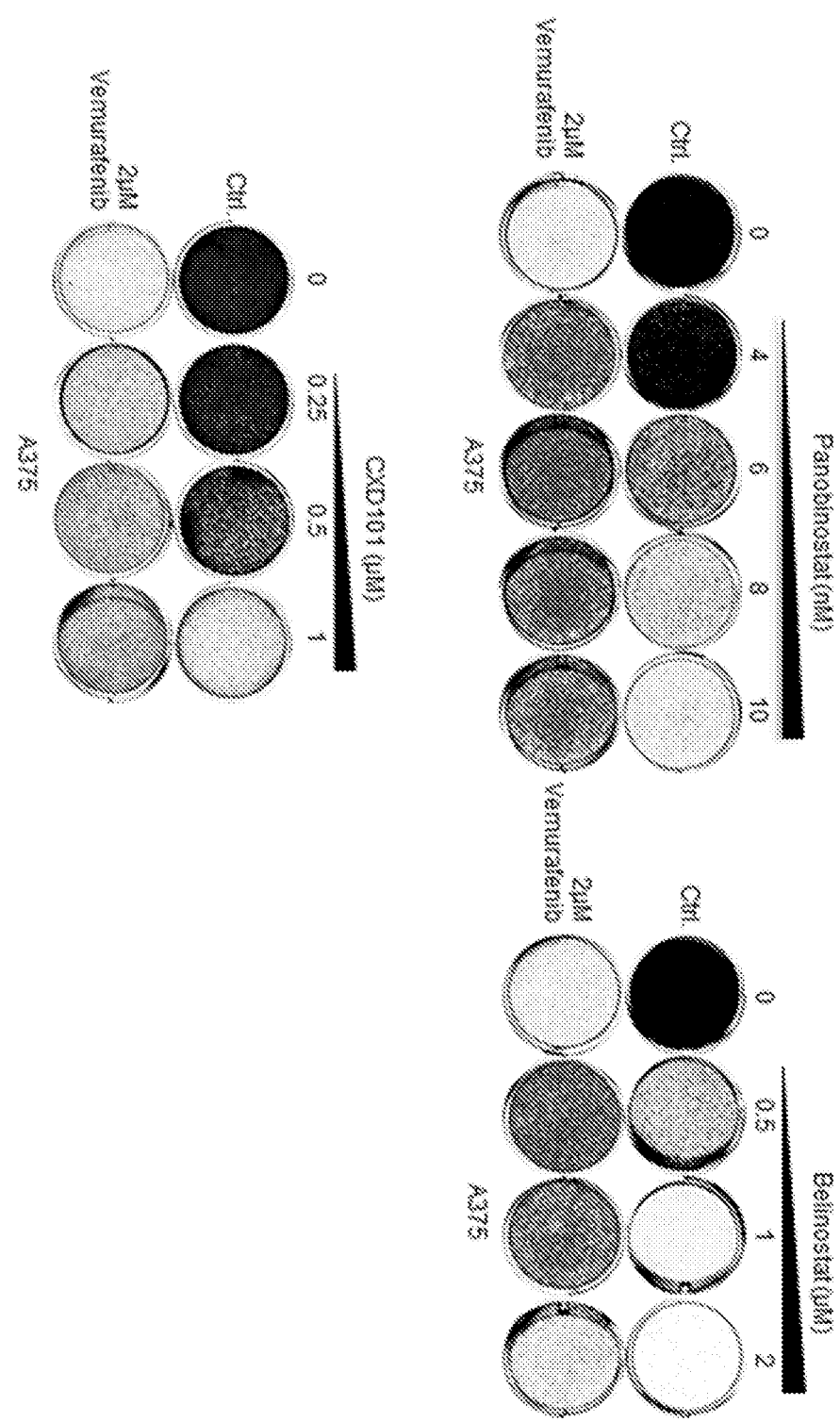
Figure 2B:
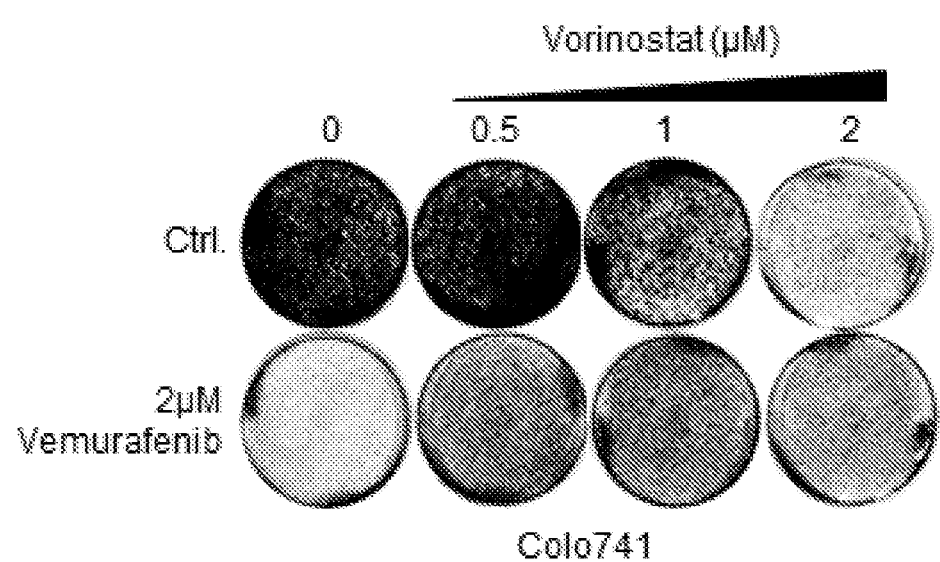

The finding that HDACi treatment further increases p-MEK levels also provides a potential explanation for the observation that vorinostat cancels the anti-proliferative effects of the BRAF inhibitor vemurafenib: While vemurafenib reduces p-MEK, vorinostat treatment increases p-MEK, thereby maintaining sufficient levels of p-MEK for the melanoma cells to proliferate. Consistent with this model, we find in A375 cells treated with either the HDACi vorinostat or entinostat increases p-MEK levels, vemurafenib reduces p-MEK, but that co-treatment with both BRAF inhibitor and HDACi results in higher steady state p-MEK levels as compared to vemurafenib monotherapy (FIG. 1 C,D). Next, we tested other HDACi to ask if this effect of vorinostat applies to the class of HDAC inhibitor drugs. FIG. 2A shows that treatment of A375 melanoma cells with panobinostat, belinostat and CXD101 was mildly anti-proliferative for these melanoma cells, but each of these HDACi conferred resistance to vemurafenib. Moreover vorinostat also conferred resistance to vemurafenib in Colo741 melanoma cells (FIG. 2B).

The current standard of care for BRAF mutant melanoma is a combination therapy with a BRAF and a MEK inhibitor. We therefore also tested whether HDACi can confer resistance to the combination of a MEK and a BRAF inhibitor in melanoma. FIG. 3 shows that the BRAF inhibitor dabrafenib, the MEK inhibitor trametinib and the combination of these two drugs were each effective in limiting proliferation of A375 cells and COL0741 cells. Importantly, the HDACi vorinostat and entinostat were each able to confer resistance to these drugs, both when used as single agents and when used in combination (FIG. 3).

HDACi Treatment is Detrimental for MAPK Pathway Inhibitor, e.g. BRAF Inhibitor, Resistant Melanoma.

Resistance to BRAF inhibition in melanoma almost invariably results from hyperactivation of MAP kinase pathway signaling (Van Allen et al., (2014) Cancer Discov 4, 94-109). Our recent data indicate that such hyperactivation of the MAP kinase pathway results in a state of growth arrest that has hallmarks of oncogene induced senescence (Sun et al., (2014) Nature 508, 118-122). However, when BRAF inhibitors are removed, this state of MAP kinase hyperactivation is rapidly counter-selected, enabling the tumor cells to proliferate again in the absence of drug. At the same time, such cells have regained sensitivity to BRAF inhibitors because the driver of resistance (hyperactivation of the MAP kinase pathway) has been lost. This phenomenon of regained drug sensitivity after a period of pause in the therapy is known as the "drug holiday effect" (Sun et al., 2014).

Figure 4A:
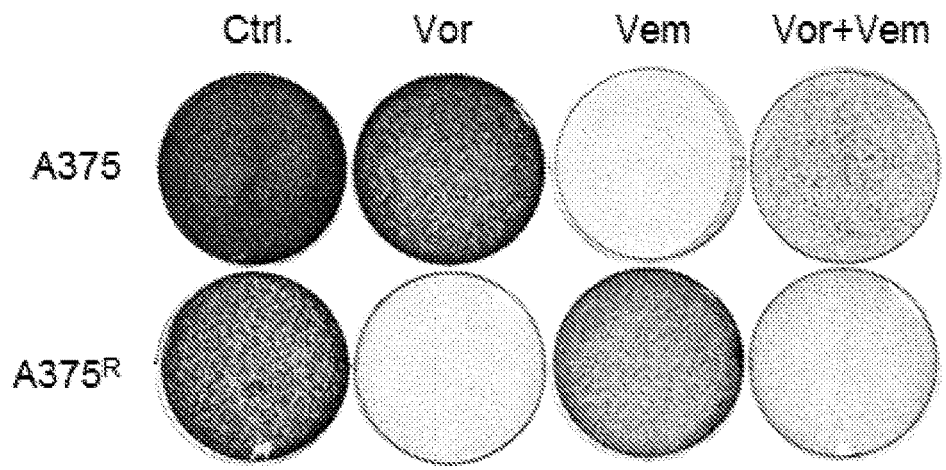
Figure 4B:
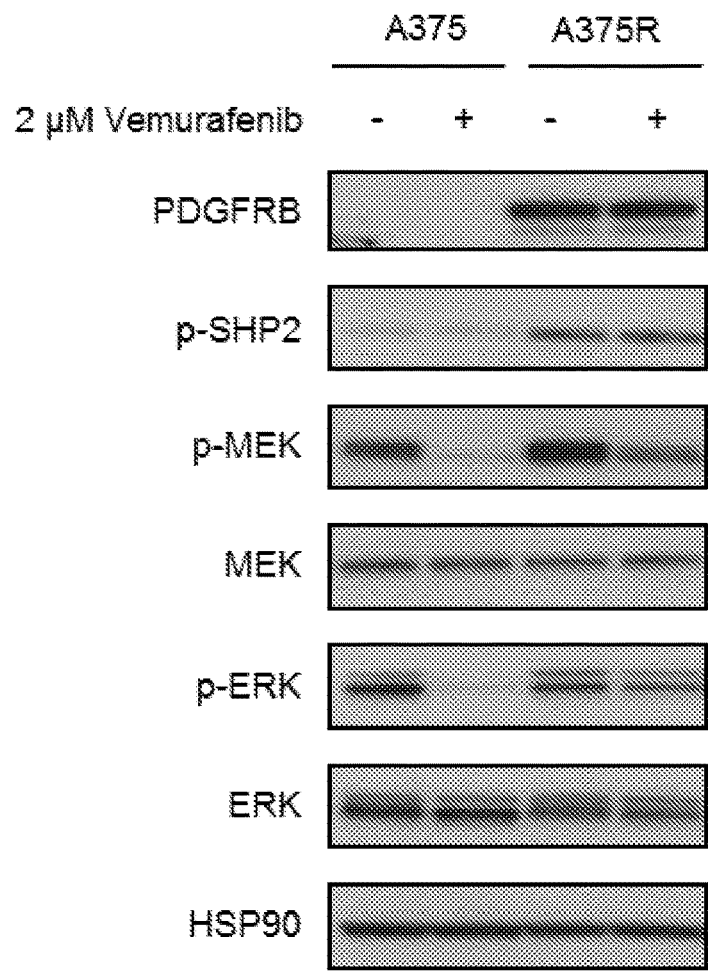
Figure 4C:
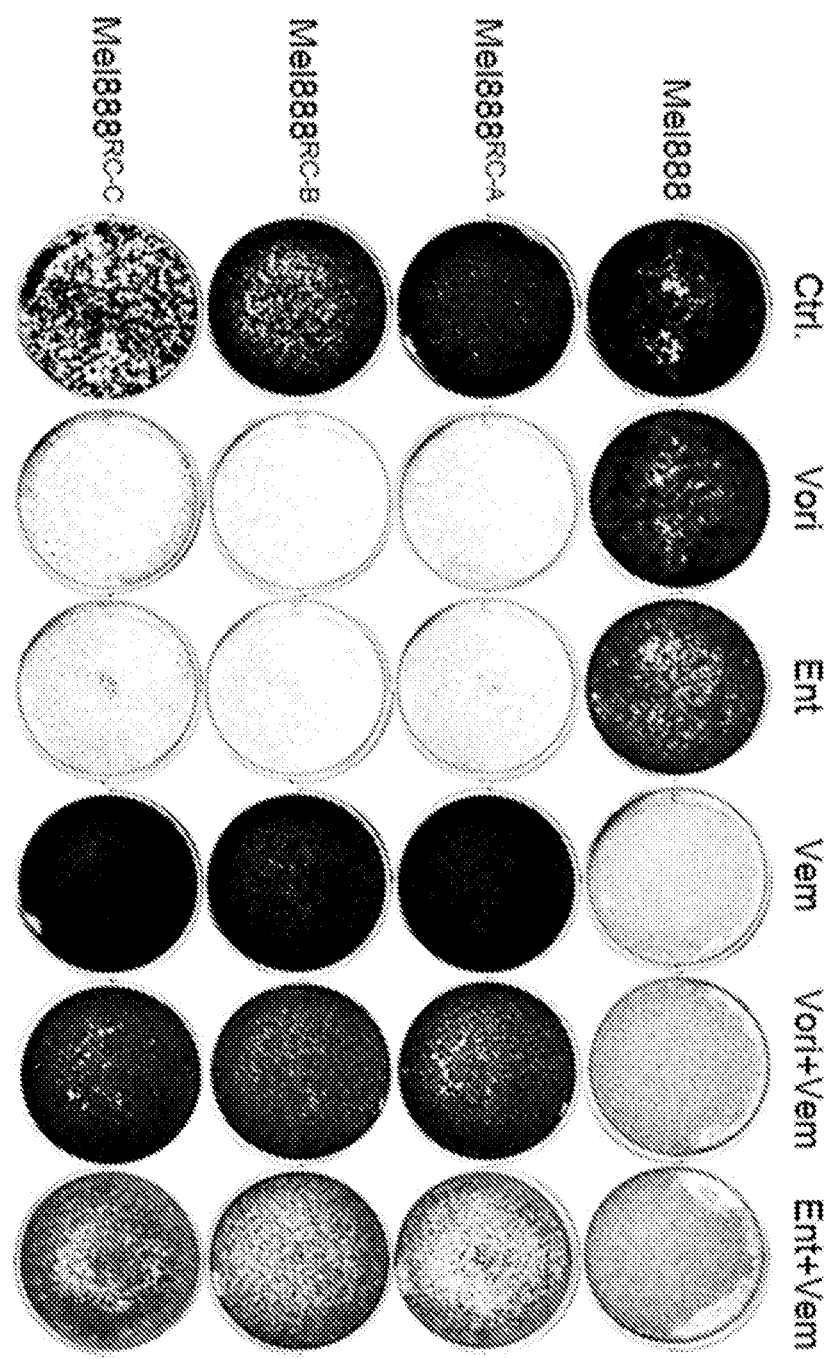

Next we made A375 melanoma cells vemurafenib resistant by long-term drug treatment. After approximately three months of continuous exposure to vemurafenib, a population of A375 cells emerged that was able to grow in the presence of vemurafenib. We named this drug resistant population A375R cells. We then treated both parental A375 cells and A375R cells with vemurafenib, vorinostat or the combination of the two drugs. FIG. 4A shows that A375R cells are resistant to vemurafenib, but far more sensitive to vorinostat than parental A375 cells, consistent with our prediction that cells with hyperactive MAP kinase signaling should have an increased vulnerability to drugs that increase MAP kinase signaling. A375R cells had increased MAP kinase signaling, as evidenced by a gain of PDGF Receptor Beta (PDGFRB) expression, increase in p-SHP2 and p-MEK (FIG. 4B). We also noted that A375R cells treated with vemurafenib maintain higher levels of p-MEK than parental A375 cells, due to hyperactivation of the MAP kinase pathway, which is only partially blocked by vemurafenib (FIG. 4B).

Similar results were obtained in BRAF mutant MEL888 cells that were made resistant to vemurafenib using the same protocol. Here again, we found that three independent clones of vemurafenib resistant MEL888 cells (MEL888RC-A, B and C) were hypersensitive to both the HDACi vorinostat and entinostat (FIG. 4C) and to CXD101 (FIG. 5).

Figure 4D:
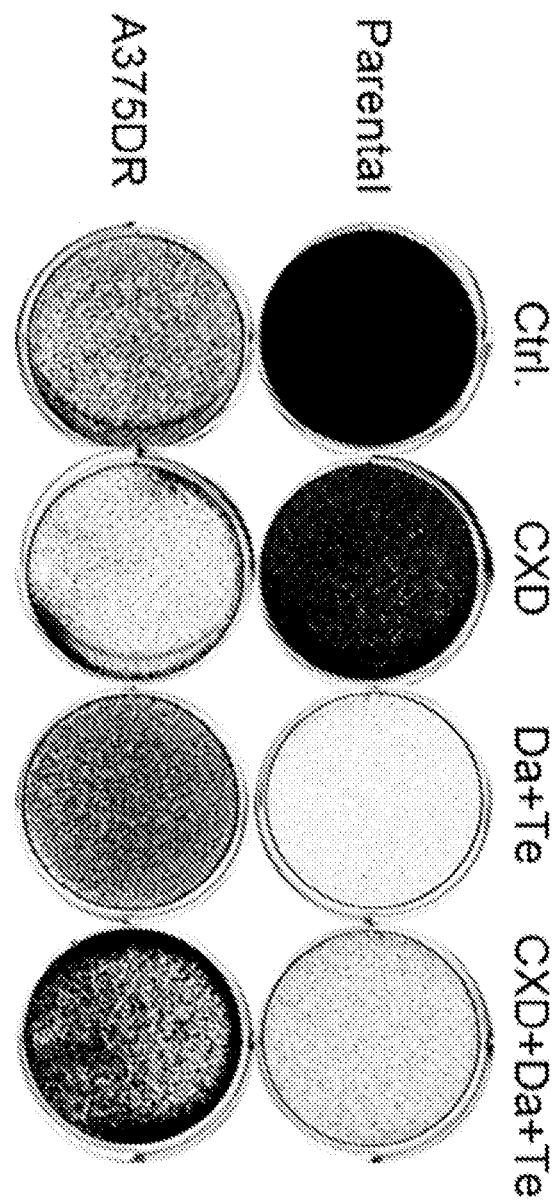

We also generated A375 cells resistant to the combination of dabrafenib and trametinib (A375DR cells). Our data indicate that these doubly resistant cells are very sensitive to the HDACi CXD101 (FIG. 4D).

To extend our observations even further to other HDACi, we treated A375 and A375R cells with Vemurafenib (Vem): 2 uM, Vorinostat (Vori): 1 uM, 01994: 4 uM, AR2: 0.5 uM, Pracinostat: 0.25 uM or Quisinostat: 25 nM in an 8 day proliferation assay. FIG. 6 shows that A375R cells are very sensitive to all HDACi tested and that the combination of vemurafenib and HDACi was less effective than the HDACi alone in these cells.

By far the strongest effects are seen when treating vemurafenib resistant melanoma cells with HDACi. Indeed, treatment of vemurafenib resistant A375R cells with vorinostat induced massive inhibition of proliferation.

Without being bound by theory we believe that treatment of MAPK pathway inhibitor resistant melanoma cell, e.g. BRAF inhibitor resistant melanoma cells (having a hyperactivated MAP kinase pathway) with an HDACi, results in the cells being unable to downregulate their state of hyperactivated MAP kinase activation and consequently maintain a state of continued proliferation arrest following the MAPK pathway inhibitor, e.g. BRAF inhibitor withdrawal.

HDACi are Effective in Treatment of BRAF Inhibitor Resistant Melanoma In Vivo.

Figure 7A:
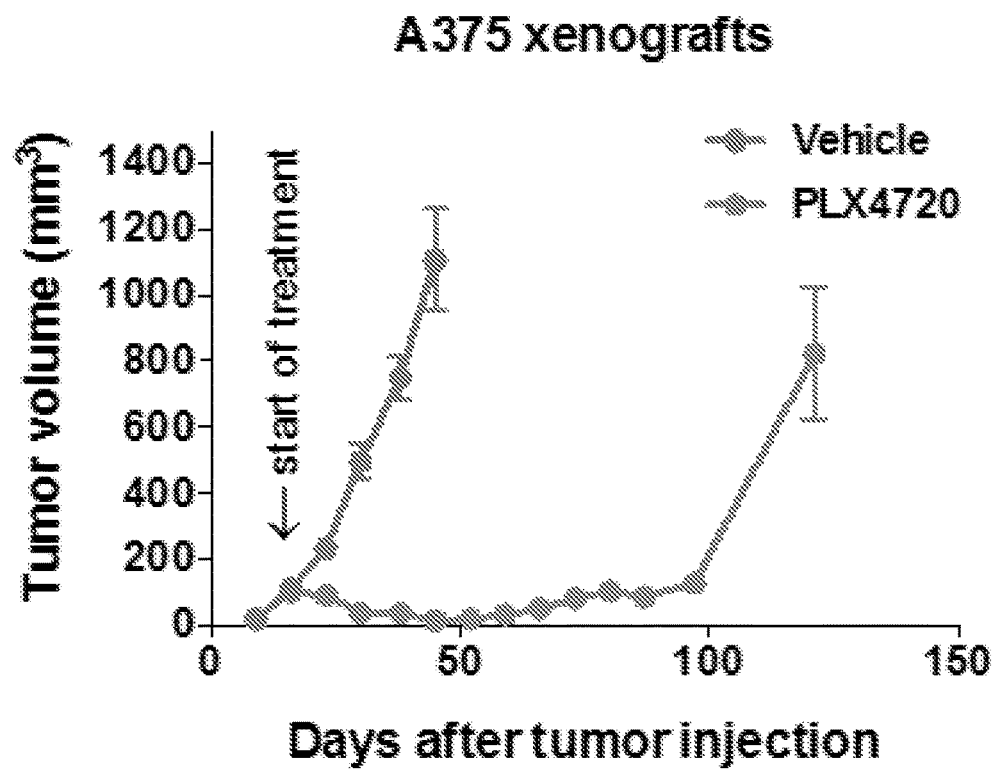

To investigate whether HDACi treatment is a suitable therapy for MPAK pathway inhibitor resistant melanoma, e.g. BRAF inhibitor resistant melanoma, we injected parental vemurafenib sensitive A375 cells into a cohort of 24 BalbC immunodeficient nude mice. After tumors had reached an average volume of 150-200 mm3, we started treatment with vemurafenib by feeding the animals chow supplemented with 40 mg/kg of PLX4720. This therapy resulted in significant suppression of tumor growth for a period of around 3 months. After that period, tumors began to increase in size, indicative of the development of drug resistance (FIG. 7A). When drug resistant tumors in the mice had reached a size of 800 mm3, mice were randomized to four cohorts that were treated either with:
A) no drug; B) PLX4270; C) PLX4270 and vorinostat; D) Vorinostat.

Figure 7B:
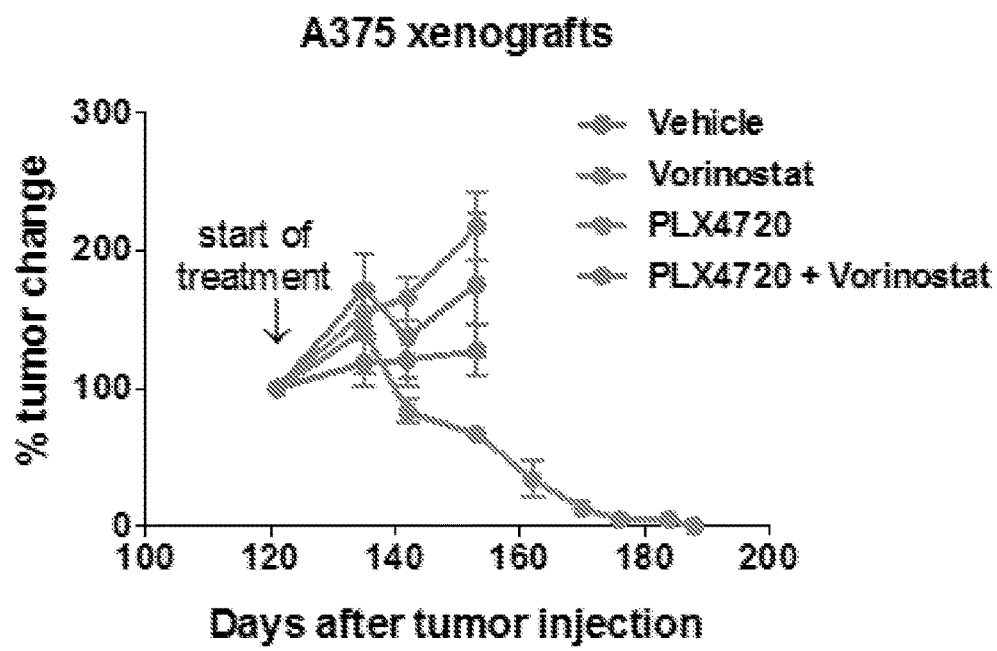

FIG. 7B shows that continued treatment of mice with BRAF inhibitor or treatment with no drug resulted in continued tumor volume increase. Treatment of cells with the combination of PLX4270 and vorinostat resulted in a slow but progressive increase in tumor volume. Most strikingly, switching the treatment of PLX4720-resistant cells from PLX4720 to vorinostat resulted in a rapid decline in tumor volume, resulting in a complete disappearance of the tumors after two months of HDACi treatment. These results are consistent with our in vitro experiments and demonstrate that HDACi treatment is most effective when used sequentially following the development of resistance to MAPK pathway inhibitors including BRAF inhibitors.

Figure 7C:
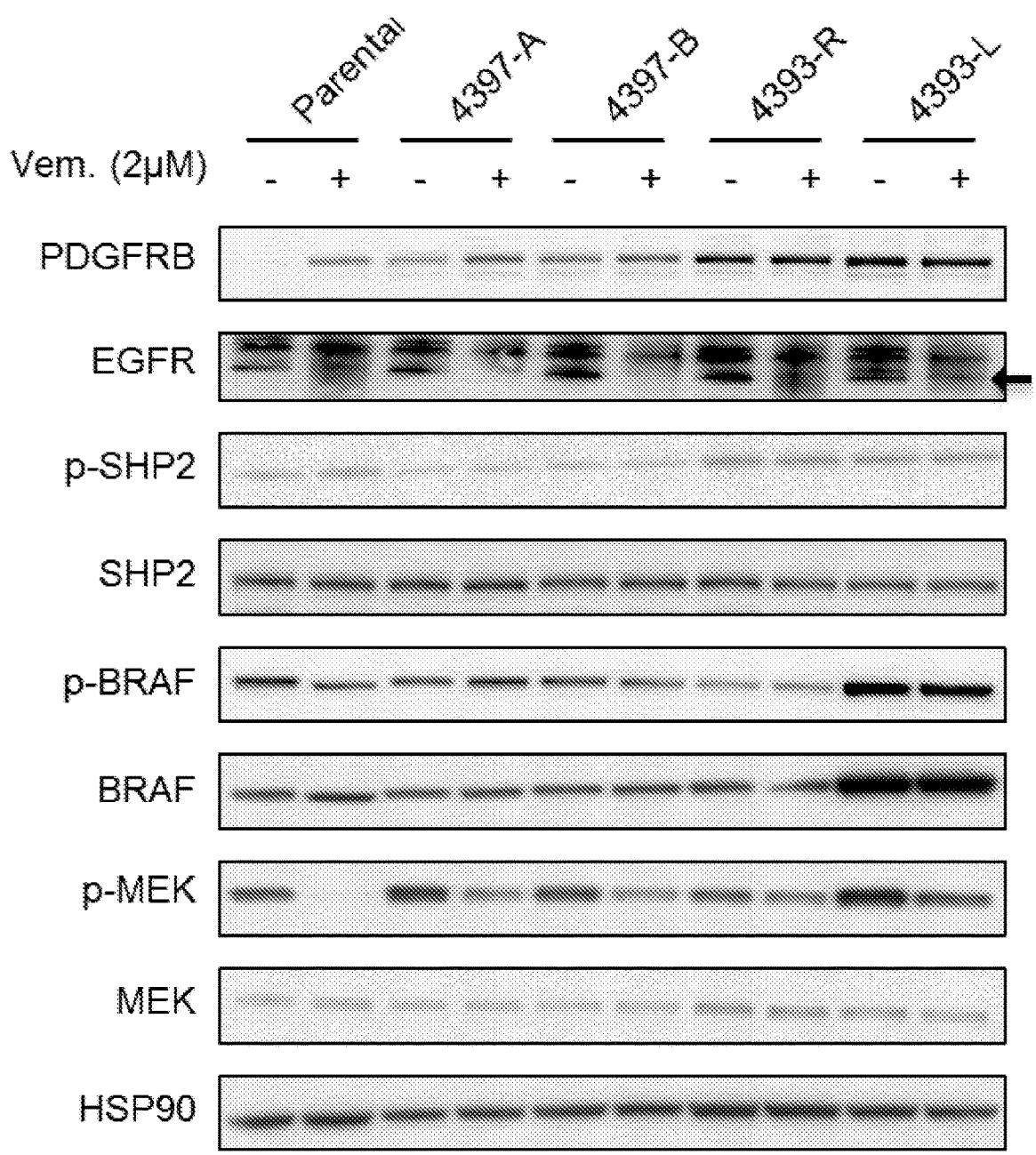

We explanted four PLX4720 resistant tumors from mice immediately after acquisition of PLX4720 resistance in vivo and continued to culture these cells in vitro in the presence of BRAF inhibitor. These cells were designated 4397A, 4397B, 4393R and 4393L. FIG. 7C shows that the parental A375 cells responded to vemurafenib by a reduction in p-MEK, but all resistant cell lines maintained significant levels of p-MEK in the presence of vemurafenib, consistent with our finding that these cells have hyperactive MAP kinase pathway signaling.

When we exposed the 4397A, 4397B, 4393R and 4393L cells to vorinostat, belinostat, panobinostat or romidepsin, all four cell lines that had developed in vivo resistance to PLX4720 were very sensitive to all HDACi, explaining why the PLX4720 resistant cells were so responsive to HDACi in vivo. Similar results were obtained with these four PLX4720 resistant cell lines following exposure to CXD101 (FIG. 8).

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding patent applications, patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

Example 2

Material and Methods
Cell Lines

The A375, SK-Mel-147 and SK-Mel-2 melanoma cell lines were obtained from ATCC. MEL888 were gifts from D. Peeper (Amsterdam, The Netherlands). All the cell lines were cultured in DMEM medium supplemented with 10% FBS, 1% penicillin/streptomycin and 2 mM I-glutamine. Vemurafenib-resistant A375 cells were generated by long term (at least 3 months) culturing with 2 µM vemurafenib. Dabrafenib-Trametinib combination resistant A375 were generated by long term (at least 3 months) culturing with 0.25 µM Dabrafenib and 10 nM Trametinib. Trametinib resistant SK-mel-147 and SK-mel-2 were generated by long term culturing with 25 nM (first month), 50 nM (second month) and 100 nM (third month) trametinib. All the in vitro cell lines have been STR profiled.

Compounds, Antibodies and Reagents

Vemurafenib (# S1267), vorinostat (# S1047), dabrafenib (# S2807), trametinib (# S2673), entinostat (# S1053), Panobinostat (# S1030), Belinostat (# S1085), Romideosin (# S3020) and Sulfasalazine (# S1576) were purchased from Selleck Chemicals. N-Acetyl-L-cysteine (A0150000 was purchased from Sigma-Aldrich.

Long-Term Cell Proliferation Assays

Cells were seeded into 6-well plates ($5*10^4 \sim 1*10^5$ cells per well) or 12-well plates ($4*10^4$ cells per well) and cultured both in the absence and presence of drugs as indicated. For full details, see ref. (Huang et al., 2009).

ROS Detection

ROS level in cells was detected using CellROX® Green Flow Cytometry Assay Kit (C10492) from Life Technologies. The detection was applied according to the manufacturer's instructions.

The primers and targeting sequence used in the experiments are described in Table 2 below.

| SEQ ID NO: | Name | Sequence (DNA) |
|---|---|---|
| 23 | Targeting sequence shSLC7A11-1 (TRCN0000043123) | CCGGCCTGTCACTATTTGGAGCTTTC TCGAGAAAGCTCCAAATAGTGACAGGTTTTTG |
| 24 | Targeting sequence shSLC7A11-2 (TRCN0000043127) | CCGGGCTGATTTATCTTCGATACAACTCG AGTTGTATCGAAGATAAATCAGCTTTTTG |
| 25 | Targeting sequence shSLC7A11-3 (TRCN0000288865) | CCGGCCTGCGTATTATCTCTTTATTCTC GAGAATAAAGAGATAATACGCAGGTTTTTG |
| 26 | Targeting sequence shSLC7A11-1 (TRCN0000380471) | GTACCGGCCCTCTATTCGGACCCATTTACT CGAGTAAATGGGTCCGAATAGAGGGTTTTTG |
| 27 | Forward primer SLC7A11 | AGCACATAGCCAATGGTGAC |
| 28 | Reverse primer SLC7A11 | GCTGGCTGGTTTTACCTCAA |

Lentiviral Constructs pLX304-SLC7A11 (CCSB-Broad Human ORF) and pLKO.1-shSLC7A11 (TRC shRNA collection) lentivirus production was performed by transfection of 2 µg of plasmid DNA into HEK cells. The viral supernatants were harvested 48 hours after transfection and filtered through a 0.45-µM filter. Melanoma cells were transduced with the virus for 24 hours, respectively. Infected cells were selected for successful retroviral integration using puromycin (for pLKO.1-shSLC7A11) and blasticidin (for pLX304-SLC7A11). shSLC7A11 targeting sequences were are described in Table 2.

Results

The present results show that NRAS mutant melanomas resistant to MEK inhibitors are also sensitive to HDACi (see FIG. 9). Melanoma is often characterized by activating mutations in BRAF (approximately 50% of patients) and NRAS (approximately 20% of patients). There are presently no approved therapies specifically targeting NRAS-mutant melanoma, but a New Drug Application for the MEK inhibitor binimetinib was recently filed by Array Biopharma based on a phase III study in NRAS mutant melanoma.

SK-MEL-147 human melanoma cells (NRAS mutant) were treated with the MEK inhibitor trametinib in vitro until resistance was observed. These SK-MEL-147R cells were then treated with vorinostat (i.e. HDACi). FIG. 9A shows that SK-MEL-147R cells are resistant to trametinib, but have at the same time acquired significant sensitivity to vorinostat compared to the parental drug sensitive SK-MEL-147 cells. The toxic effect of vorinostat in SK-MEL-147R cells was rescued by the ROS scavenger N-acetyl cysteine (NAC), indicating that increased ROS levels may be instrumental in the toxic effect of vorinostat on SK-MEL-147R cells (FIG. 9B).

We also observed that vorinostat treatment resulted in reduced XCT (also known as SLC7A11) mRNA expression in SK-MEL-147R cells (FIG. 9D), which may explain their increased ROS levels (FIG. 9E).

Ectopic expression of the cDNA encoding XCT (also known as SLC7A11) (shown in FIG. 9G) rescued the toxic effects of HDAC inhibition (FIG. 9F), consistent with the notion that XCT (also known as SLC7A11) may antagonize the increase in ROS levels caused by HDACi treatment. This notion is supported by measurement of ROS levels in SK-MEL-147R cells that express increased levels of SLC7A11 (FIG. 9H).

Similar results were obtained in a second NRAS mutant human melanoma cell line SK-MEL-2. Again, MEK inhibitor resistant variants of this cell line (named SK-MEL-2R) were more sensitive to vorinostat (FIG. 9I), and the toxic effects of vorinostat in these cells were countered, at least in part, by treatment with ROS scavenger NAC (FIG. 9J). Together, these results indicate that treatment of MAPk pathway inhibitor, e.g. MEK inhibitor, resistant NRAS mutant melanoma cells with vorinostat (HDACi) has significant anti-cancer effects.

Example 3

Materials and Methods

The materials and methods for example 3 is the same as in example 2 above.

Results

The results show that HDAC inhibitors increase Reactive Oxygen Species (ROS) via down-regulation of SCL7A11 (see FIG. 10).

To study how treatment with histone deacetylases inhibitors (HDACi) may cause an increase in ROS in melanoma cells, we performed global gene expression analysis. We used three cell lines for this experiment:
1) A375 cells: BRAF mutant human melanoma cells sensitive to BRAF inhibitors.
2) A375R cells: BRAF mutant human melanoma cells resistant to BRAF inhibitors.
3) A375DR cells: BRAF mutant human melanoma cells resistant to a combination of BRAF and MEK inhibitors.

Cells were treated for 72 hours with the HDACi vorinostat and RNA was extracted for transcriptome analysis using RNAseq. The results of these experiments revealed an unexpected down-regulation of the cystine-glutamate antiporter referred to as XCT (also known as SLC7A11) after HDACi treatment.

XCT serves as a transmembrane transporter that is capable of importing cystine into the cell, which serves as a precursor to reduced glutathione (GSH), which is required to inactivate ROS. Thus, downregulation of XCT (also known as SLC7A11) could explain increased ROS levels caused by HDACi, as reduced abundance of this protein reduces GSH levels, which leads to an increase in ROS.

In order to validate this finding, we performed quantitative PCR (Q-PCR) on A375 cells, A375R cells and A375DR cells both before and after treatment with vorinostat. FIG. 10A shows that XCT (also known as SLC7A11) was upregulated during drug resistance, but in each case, vorinostat treatment reduced XCT (also known as SLC7A11) expression. To validate whether the reduction in XCT expression would result in an increase in ROS levels, we knocked down the SLC7A11 gene (which encodes XCT) using shRNA and monitored ROS levels in the knockdown cells (targeting sequence are shown in Table 2). FIGS. 10B and C show that there is a direct correlation between reduction in XCT (also known as SLC7A11) expression and an increase in ROS, as measured by CellROX Green (FIG. 10C). Having established that knockdown of XCT (also known as SLC7A11) causes an increase in ROS, we argued that knockdown of this gene should be more toxic to A375R and A375DR cells, as these cells already have increased ROS levels compared to parental A375 cells. Indeed, FIG. 10D shows that knockdown of XCT (also known as SLC7A11) with three different shRNAs (see table 2 for targeting construct) had a more dramatic effect on cell proliferation (i.e. cause more cell death or less cell survival) in A375R and A375 DR cells compared to parental A375 cells. Conversely, when we expressed the cDNA encoding XCT (i.e. SCL7A11) in A375R or A375DR cells, we rescued the toxic effect of vorinostat, likely due to the reduction in ROS levels (FIGS. 10 E and F).

Further, over-expression of XCT (also known as SCL7A11) gene was verified by quantitative PCR (FIG. 10G) and this increase in XCT (also known as SLC7A11) antagonizes the increase in ROS levels caused by vorinostat treatment (FIG. 10H).

Several inhibitors of XCT (also known as SLC7A11) have been developed for various disease indications, including sulfasalazine, which is marketed under the trade name Azulfidine and used to treat rheumatoid arthritis. Since our data indicate that suppression of the expression of XCT (i.e. SLC7A11) is toxic to A375R and A375DR cells, we argued that inhibition of XCT (i.e. SLC7A11) may have a similar effect through increased ROS levels in the cells. Indeed, FIG. 11 shows that treatment of A375 cells, A375R cells and A375DR cells with concentrations of sulfasalazine ranging from 0.2 to 0.4 mM was toxic primarily to A375R and A375DR cells. Importantly, co-treatment of the latter two cell lines with vorinostat (HDACi) and sulfasalazine (XCT inhibitor) resulted in synergistic toxicity (i.e. cause more cell death or cause greater decrease in cell survival), most likely due to the fact that both compounds increase ROS levels in these cells.

The invention claimed is:

1. A method of treating a subject with melanoma characterized in that the melanoma is a BRAF-mutation or a NRAS-mutation harboring melanoma, the method comprising:
   a) Treating said subject with a therapeutically acceptable amount of a MAPK pathway inhibitor, wherein the treatment with the MAPK pathway inhibitor does not involve a simultaneous treatment with an HDACi;
   b) Discontinuing treating the subject with said therapeutically acceptable amount of the MAPK pathway inhibitor when the melanoma has acquired resistance to the MAPK pathway inhibitor;
   c) Treating said subject with a therapeutically acceptable amount of a histone deacytylase inhibitor (HDACi) after treatment with MAPK pathway inhibitor is discontinued in step b).

2. The method of claim 1 wherein step c) starts 1-28 days after step b).

3. The method of claim 1, wherein the treatment with HDACi is in combination with the treatment with a XCT inhibitor (XCTi).

4. The method of claim 3, wherein the XCTi is selected from sulfasalazine and erastin.

5. The method of claim 1, wherein the HDACi is vorinostat, CXD-101, entinostat, C1994, AR42, practinostat, quisinostat, panobinostat, belinostat romidepsin or combinations thereof.

6. The method of claim 1, wherein the MAPK pathway inhibitor the melanoma has acquired resistance to is a RAS inhibitor, a RAF inhibitor, a MEK inhibitor, an ERK inhibitor and/or a RSK inhibitor.

7. The method of claim 6, wherein the RAS inhibitor, RAF inhibitor, MEK inhibitor, ERK inhibitor and/or a RSK inhibitor is vemurafenib, dabrafenib, trametinib, LGX-818, cobimetinib, binimetinib, selumetinib, PD-0325901, MEK162, SCH772984, or combinations thereof.

* * * * *

```
                              SEQUENCE LISTING

<160> NUMBER OF SEQ ID NOS: 28

<210> SEQ ID NO 1
  <211> LENGTH: 20
  <212> TYPE: DNA
  <213> ORGANISM: Artificial Sequence
  <220> FEATURE:
  <223> OTHER INFORMATION: synthetic

<400> SEQUENCE: 1
tcctctggag gctgagaaaa                                                     20

<210> SEQ ID NO 2
  <211> LENGTH: 20
  <212> TYPE: DNA
  <213> ORGANISM: Artificial Sequence
  <220> FEATURE:
  <223> OTHER INFORMATION: primer

<400> SEQUENCE: 2
gggctctgga ggaaaagaaa                                                     20

<210> SEQ ID NO 3
  <211> LENGTH: 20
  <212> TYPE: DNA
  <213> ORGANISM: Artificial Sequence
  <220> FEATURE:
  <223> OTHER INFORMATION: primer

<400> SEQUENCE: 3
aaggtgaagg tcggagtcaa                                                     20

<210> SEQ ID NO 4
  <211> LENGTH: 20
  <212> TYPE: DNA
  <213> ORGANISM: Artificial Sequence
  <220> FEATURE:
  <223> OTHER INFORMATION: primer

<400> SEQUENCE: 4
aatgaagggg tcattgatgg                                                     20

<210> SEQ ID NO 5
  <211> LENGTH: 20
  <212> TYPE: DNA
  <213> ORGANISM: Artificial Sequence
  <220> FEATURE:
  <223> OTHER INFORMATION: primer

<400> SEQUENCE: 5
ctttcttgtg ctgcatacgg                                                     20

<210> SEQ ID NO 6
  <211> LENGTH: 18
  <212> TYPE: DNA
  <213> ORGANISM: Artificial Sequence
  <220> FEATURE:
  <223> OTHER INFORMATION: primer

<400> SEQUENCE: 6
agctcagcaa gacgctgg                                                       18
```

```
<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
caggagagac agcaacagca                                                 20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
tgtccagagc ctggaactgt                                                 20

<210> SEQ ID NO 9
<211> LENGTH: 23
<212> TYPE: DNA
<213> ORGANISM: Artificial Sequence
<220> FEATURE:
<223> OTHER INFORMATION: primer

<400> SEQUENCE: 9
cgactctgat tagtcggaac tca                                             23

<210> SEQ ID NO 10
<211> LENGTH: 21
<212> TYPE: DNA
<213> ORGANISM: Artificial Sequence
<220> FEATURE:
<223> OTHER INFORMATION: primer

<400> SEQUENCE: 10
ggtggttgta gtcatccaag c                                               21

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
tctggttgtc acaggtggaa                                                 20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
gcacgttcag aagtcggtta                                                 20

<210> SEQ ID NO 13
<211> LENGTH: 20
<212> TYPE: DNA
<213> ORGANISM: Artificial Sequence
<220> FEATURE:
<223> OTHER INFORMATION: primer
```

```
<400> SEQUENCE: 13
gtccgaaccc agacacaagt                                               20

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
ctcatgccat aggaaggacc                                               20

<210> SEQ ID NO 15
<211> LENGTH: 18
<212> TYPE: DNA
<213> ORGANISM: Artificial Sequence
<220> FEATURE:
<223> OTHER INFORMATION: primer

<400> SEQUENCE: 15
gctggaatgc aacttcgg                                                 18

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
cccgttttgg tagattctgg                                               20

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
taccaatgac aacgcctcct                                               20

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
tggagatttt gggagtacgg                                               20

<210> SEQ ID NO 19
<211> LENGTH: 19
<212> TYPE: DNA
<213> ORGANISM: Artificial Sequence
<220> FEATURE:
<223> OTHER INFORMATION: primer

<400> SEQUENCE: 19
ggaacagctc ctggcaatc                                                19

<210> SEQ ID NO 20
```

-continued

```
<211> LENGTH: 20
<212> TYPE: DNA
<213> ORGANISM: Artificial Sequence
<220> FEATURE:
<223> OTHER INFORMATION: primer

<400> SEQUENCE: 20
gcacctagac catgaggtgg                                              20

<210> SEQ ID NO 21
<211> LENGTH: 19
<212> TYPE: DNA
<213> ORGANISM: Artificial Sequence
<220> FEATURE:
<223> OTHER INFORMATION: primer

<400> SEQUENCE: 21
gtggattatg ctccccacc                                               19

<210> SEQ ID NO 22
<211> LENGTH: 17
<212> TYPE: DNA
<213> ORGANISM: Artificial Sequence
<220> FEATURE:
<223> OTHER INFORMATION: primer

<400> SEQUENCE: 22
ctgccattcc ggaggag                                                 17

<210> SEQ ID NO 23
<211> LENGTH: 58
<212> TYPE: DNA
<213> ORGANISM: Artificial sequence
<220> FEATURE:
<223> OTHER INFORMATION: Targetting sequence

<400> SEQUENCE: 23
ccggcctgtc actatttgga gctttctcga gaaagctcca aatagtgaca ggttttttg   58

<210> SEQ ID NO 24
<211> LENGTH: 58
<212> TYPE: DNA
<213> ORGANISM: Artificial sequence
<220> FEATURE:
<223> OTHER INFORMATION: Targeting sequence

<400> SEQUENCE: 24
ccgggctgat ttatcttcga tacaactcga gttgtatcga agataaatca gcttttttg  58

<210> SEQ ID NO 25
<211> LENGTH: 58
<212> TYPE: DNA
<213> ORGANISM: Artificial sequence
<220> FEATURE:
<223> OTHER INFORMATION: Targeting sequence

<400> SEQUENCE: 25
ccggcctgcg tattatctct ttattctcga gaataaagag ataatacgca ggttttttg  58

<210> SEQ ID NO 26
<211> LENGTH: 62
<212> TYPE: DNA
<213> ORGANISM: Artificial sequence
<220> FEATURE:
<223> OTHER INFORMATION: Targeting sequence

<400> SEQUENCE: 26
```

```
gtaccggccc tctattcgga cccatttact cgagtaaatg ggtccgaata gagggttttt    60
tg                                                                   62

<210> SEQ ID NO 27
<211> LENGTH: 20
<212> TYPE: DNA
<213> ORGANISM: Artificial sequence
<220> FEATURE:
<223> OTHER INFORMATION: Forward primer

<400> SEQUENCE: 27
agcacatagc caatggtgac                                                20

<210> SEQ ID NO 28
<211> LENGTH: 20
<212> TYPE: DNA
<213> ORGANISM: Artificial sequence
<220> FEATURE:
<223> OTHER INFORMATION: Reverse primer

<400> SEQUENCE: 28
gctggctggt tttacctcaa                                                20
```